US012599598B2

(12) United States Patent
Shah et al.

(10) Patent No.: US 12,599,598 B2
(45) Date of Patent: ***Apr. 14, 2026

(54) OSMOTIC DOSAGE FORMS COMPRISING DEUTETRABENAZINE AND METHODS OF USE THEREOF

(71) Applicant: Auspex Pharmaceuticals, Inc., Parsippany, NJ (US)

(72) Inventors: Parag Shah, Weston, FL (US); Mayank Joshi, Weston, FL (US); Soumen Pattanayek, Weston, FL (US); Divyang Patel, Weston, FL (US); Sandeep Pandita, Parsippany, NJ (US)

(73) Assignee: AUSPEX PHARMACEUTICALS LLC, Parsippany, NJ (US)

( * ) Notice: Subject to any disclaimer, the term of this patent is extended or adjusted under 35 U.S.C. 154(b) by 874 days.

This patent is subject to a terminal disclaimer.

(21) Appl. No.: 17/835,435

(22) Filed: Jun. 8, 2022

(65) Prior Publication Data

US 2022/0296585 A1 Sep. 22, 2022

Related U.S. Application Data

(63) Continuation-in-part of application No. 17/344,271, filed on Jun. 10, 2021, now Pat. No. 11,311,488.

(60) Provisional application No. 63/044,451, filed on Jun. 26, 2020, provisional application No. 63/037,953, filed on Jun. 11, 2020, provisional application No. 63/037,369, filed on Jun. 10, 2020.

(51) Int. Cl.
| | |
|---|---|
| *A61K 9/00* | (2006.01) |
| *A61K 9/20* | (2006.01) |
| *A61K 31/4745* | (2006.01) |

(52) U.S. Cl.
CPC ........ *A61K 31/4745* (2013.01); *A61K 9/0004* (2013.01); *A61K 9/0053* (2013.01); *A61K 9/2077* (2013.01)

(58) Field of Classification Search
None
See application file for complete search history.

(56) References Cited

U.S. PATENT DOCUMENTS

| | | | |
|---|---|---|---|
| 3,173,876 A | 3/1965 | Zobrist | |
| 3,276,586 A | 10/1966 | Rosaen | |
| 3,541,005 A | 11/1970 | Strathmann | |
| 3,541,006 A | 11/1970 | Bixler | |
| 3,546,142 A | 12/1970 | Amicon | |
| 3,845,770 A | 11/1974 | Theeuwes et al. | |
| 3,916,899 A | 11/1975 | Theeuwes et al. | |
| 4,088,864 A | 5/1978 | Saunders | |
| 4,200,098 A | 4/1980 | Ayer | |
| 4,327,725 A | 5/1982 | Cortese et al. | |
| 4,612,008 A | 9/1986 | Wong et al. | |
| 4,783,337 A | 11/1988 | Wong et al. | |
| 5,082,668 A | 1/1992 | Wong et al. | |
| 8,524,733 B2 | 9/2013 | Gant et al. | |
| 9,296,739 B2 | 3/2016 | Sommer et al. | |
| 2003/0161882 A1 | 8/2003 | Waterman | |
| 2007/0031496 A1* | 2/2007 | Edgren | A61K 9/0004 |
| | | | 424/473 |
| 2012/0208773 A1 | 8/2012 | Duffield et al. | |
| 2013/0323309 A1* | 12/2013 | Bhutada | A61K 9/5073 |
| | | | 424/490 |
| 2017/0087147 A1* | 3/2017 | Sommer | A61K 9/284 |
| 2018/0263972 A1 | 9/2018 | Zhang et al. | |
| 2018/0318281 A1* | 11/2018 | Stamler | A61K 31/473 |
| 2020/0289498 A1 | 9/2020 | Sommer et al. | |
| 2020/0360354 A1 | 11/2020 | Liang et al. | |

FOREIGN PATENT DOCUMENTS

| | | |
|---|---|---|
| CN | 104684555 A | 6/2015 |
| JP | 2009-507774 A | 2/2009 |
| JP | 2013-501810 A | 1/2013 |
| JP | 2015-528516 A | 9/2015 |
| WO | 2011/019956 A2 | 2/2011 |
| WO | 2017/182916 A1 | 10/2017 |
| WO | 2021/252741 A1 | 12/2021 |

OTHER PUBLICATIONS

Almoshari, Osmotic Pump Drug Delivery Systems—A Comprehensive Review, Pharmaceuticals, 2022, 15(11):1430.

Ogueri et al., "Osmotic-controlled release oral tablets: technology and functional insights", Trends in Biotechnology, May 2022, vol. 40, No. 5, 606-619.

Tarakad et al., "VMAT2 Inhibitors in Neuropsychiatric Disorders", CNS Drugs, 2018, 32 (12), 1131-1144.

Dean et al., "Review of deutetrabenazine: a novel treatment for chorea associated with Huntington's disease," Drug Des Devel. Ther., Feb. 15, 2018, 12, pp. 313-319.

* cited by examiner

*Primary Examiner* — Susan T Tran
(74) *Attorney, Agent, or Firm* — BakerHostetler

(57) ABSTRACT

Provided herein are osmotic dosage forms containing deutetrabenazine for use in the treatment of, e.g., hyperkinetic movement disorders. When orally administered to a subject on a once-daily basis, the dosage forms provide a favorable pharmacokinetic profile for the active agent indicating treatment efficacy over an extended period of time.

7 Claims, 8 Drawing Sheets

1

OSMOTIC DOSAGE FORMS COMPRISING DEUTETRABENAZINE AND METHODS OF USE THEREOF

CROSS REFERENCE TO RELATED APPLICATIONS

This application is a continuation in part of U.S. application Ser. No. 17/344,271, filed Jun. 10, 2021, which claims the benefit of U.S. Provisional Application Nos. 63/037,369, filed Jun. 10, 2020, 63/037,953, filed Jun. 11, 2020, and 63/044,451 filed Jun. 26, 2020, the entireties of which are incorporated by reference herein.

TECHNICAL FIELD

The present disclosure pertains to osmotic dosage forms and methods of use of those dosage forms for treating hyperkinetic movement disorders deriving from conditions such as Huntington's disease, tardive dyskinesia, Tourette syndrome, levodopa-induced dyskinesia and dyskinesia in cerebral palsy.

BACKGROUND

Deutetrabenazine ((RR,SS)-1,3,4,6,7,11b-hexahydro-9,10-di(methoxy-d3)-3-(2-methylpropyl)-2H-benzo[a]quinolizin-2-one) is a vesicular monoamine transporter type 2 (VMAT2). The biologically active metabolites formed from deutetrabenazine (alpha-dihydrodeutetrabenazine [α-deuHTBZ] and beta-dihydrodeutetrabenazine [β-deuHTBZ]), together identified as "deuHTBZ", are potent inhibitors of VMAT2 binding. Deutetrabenazine exhibits an increased half-life of its active metabolites, relative to tetrabenazine (e.g., U.S. Pat. No. 8,524,733).

Deutetrabenazine is approved by the U.S. Food and Drug Administration under the tradename AUSTEDO® for the treatment of chorea (involuntary muscle movements) associated with Huntington's disease (HD) and for the treatment of tardive dyskinesia (TD) in adults. AUSTEDO® dosage forms are orally administered twice-daily (bid), for total daily doses of 12 mg or above of deutetrabenazine.

One factor affecting gastrointestinal absorption of orally administered drugs is the rate at which drug is released from the dosage form. Drug release rates for oral dosage forms are typically measured as rate of dissolution in vitro, i.e., a quantity of drug released from the dosage form per unit time for example, in a FDA approved system. Such systems include, for example, United States Pharmacopeia (USP) dissolution apparati I and II.

The therapeutic window of a drug is the time period when the plasma drug concentration is within the therapeutically effective plasma drug concentration range. Because the plasma drug concentration declines over time, however, multiple doses of drug dosage form must be administered at appropriate intervals to ensure that the plasma drug concentration remains within or, again rises to, the therapeutic window. At the same time, however, there is a need to avoid or minimize plasma drug concentrations that result in undesirable side effects.

Several dosage forms comprising deutetrabenazine are disclosed in U.S. Pat. No. 9,296,739. A dosage form that can deliver deutetrabenazine in a controlled manner over an extended period of time would enable a more advantageous dosing regimen, e.g., one that would permit once-daily (qd) administration while maintaining the treatment effects currently realized by AUSTEDO®. A need exists for such alternative dosage forms.

SUMMARY

Disclosed herein are osmotic dosage forms for once daily administration of deutetrabenazine to a subject in need thereof comprising:
- a. a tablet core comprising an active layer comprising an amount of deutetrabenazine microparticles and a push layer;
- b. a semipermeable layer surrounding the tablet core; and
- c. a port extending through the semipermeable layer into the tablet core.

Further disclosed herein are methods of treating a hyperkinetic movement disorder in a subject comprising: administering on a once daily basis to the subject an osmotic dosage form disclosed herein.

BRIEF DESCRIPTION OF THE DRAWINGS

FIG. 3a shows direct scale for mean concentration, and FIG. 3b shows a log scale for mean concentration.

FIG. 4a shows direct scale for mean concentration, and FIG. 4b shows a log scale for mean concentration.

DETAILED DESCRIPTION

Figure 1:
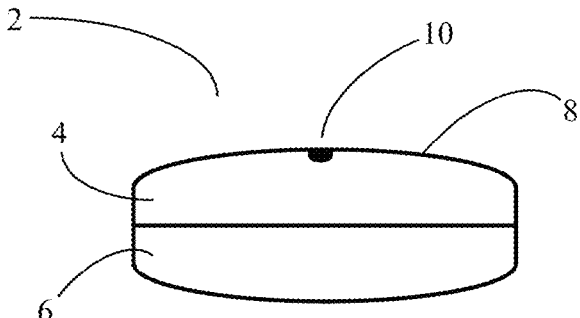
FIG. 1 provides an illustration of an osmotic dosage form in cross-section.

The present subject matter may be understood more readily by reference to the following detailed description, which forms a part of this disclosure. It is to be understood that this invention is not limited to the specific methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a", "an", and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "compound", "drug", "pharmacologically active agent", "active agent", or "medicament" are used interchangeably herein to refer to a compound or compounds or composition of matter which, when administered to a subject (human or animal) induces a desired pharmacological and/or physiologic effect by local and/or systemic action. The active agent is preferably deutetrabenazine, as disclosed herein.

As used herein, "dosage form" refers to a drug form having osmotic properties and able to release active agent over an extended period, for example, the dosage form releases not more than 60 wt % of the active agent in the dosage form for 8 hours after administration. The active agent is preferably deutetrabenazine, as disclosed herein.

As used herein, the term "drug formulation" refers to a solution or suspension of the drug, optionally with excipients, formed in situ under aqueous conditions of the dosage form. The active agent is preferably deutetrabenazine, as disclosed herein.

The terms "port" or "exit port", used interchangeably, refer to means and methods suitable for exit of the drug or the drug formulation from the core of the dosage form, for example, any hole, passage, channel or similar opening though which the drug or the drug formulation in the core of the dosage form may exit. Other expressions of such term include, for example, exit means, orifice or hole.

As used herein, the terms "treatment" or "therapy" (as well as different forms thereof) include preventative (e.g., prophylactic), curative, or palliative treatment. As used herein, the term "treating" includes alleviating or reducing at least one adverse or negative effect or symptom of a condition, disease or disorder. This condition, disease or disorder may refer to hyperkinetic movement disorder, such as, but not limited to, Huntington's disease, tardive dyskinesia, Tourette syndrome, dystonia, dyskinesia in cerebral palsy and Parkinson's disease levodopa-induced dyskinesia.

The term "administering" means providing to a patient a pharmaceutical composition or dosage form (used interchangeably herein) disclosed herein.

The terms "subject", "individual", and "patient" are used interchangeably herein, and refer to a human, to whom treatment, including prophylactic treatment, with a dosage form disclosed herein, is provided.

"Pharmaceutically acceptable" refers to those compounds, materials, compositions, and/or excipients which are, within the scope of sound medical judgment, suitable for contact with the tissues of human beings without excessive toxicity, irritation, allergic response, or other problem complications commensurate with a reasonable benefit/risk ratio.

The presently disclosed dosage forms may include "derivatives" of certain dosage form materials or ingredients, such as derivatives of cellulose or starch. As used herein, a "derivative" of a material may refer to a synthetic or semi-synthetic product of that material. For example, in the case of cellulose, a derivative can refer to semi-synthetic cellulose products such as cellophane, rayon, and cellulose acetate, cellulose esters, and cellulose ethers.

"Microparticles" refers to particles, for example deutetrabenazine particles, with a particle size (i.e. diameter) below 1 mm. In one embodiments, the median diameter ($D_{50}$) of the microparticles is from about 0.05 to about 100 μm. In another embodiment, $D_{50}$ of the microparticles is from about 0.05 to about 50 μm. In another embodiment, the $D_{50}$ of the microparticles is from about 1 μm to about 30 μm, or about 1 μm to about 25 μm, or about 5 μm to about 30 μm, or about 1 μm to about 20 μm, or about 5 μm to about 25 μm, or about 10 μm to about 20 μm. In one embodiment, the deutetrabenazine microparticles have a particle size distribution of about 1 μm to about 30 μm in diameter. In another embodiment, the deutetrabenazine microparticles have a $D_{90}$ of 15 μm (i.e. 90% of the particles have a diameter less than or equal to 15 um). In another embodiment, the deutetrabenazine microparticles have a $D_{50}$ 10 μm (i.e. 50% of the particles have a diameter greater than 10 um and 50% of the particles have a diameter less than or equal to 10 um). In yet another embodiment, the deutetrabenazine microparticles have a $D_{10}$ of 3 μm (i.e. 10% of the particles have a diameter less than 3 um).

The terms $D_{90}$, $D_{50}$ or $D_{10}$ are well understood in the art. The particle size distribution of the microparticles (i.e. the diameters) can be determined by one with skill in art using conventional methods, for example, dynamic or static light-scattering of an aqueous dispersion of the microparticle composition. The $D_{90}$ and $D_{10}$ values, like the $D_{50}$ value, can be calculated from the particle size distribution of the microparticles.

Osmotic dosage forms, in general, utilize osmotic pressure to generate a driving force for imbibing fluid, for example, from the gastrointestinal (GI) tract, into a compartment formed, at least in part, by a semipermeable wall, layer or membrane that permits free diffusion of fluid but not drug or osmotic agent(s), if present. A constant rate of drug release can be achieved by designing the system to provide a relatively constant osmotic pressure and having suitable exit means for the drug formulation to be released at a rate that corresponds to the rate of fluid imbibed as a result of the relatively constant osmotic pressure. Without being limited to theory, osmotic systems may operate independently of pH and thus, operation continues at the osmotically-determined rate throughout an extended time period even as the dosage form transits the GI tract and encounters differing microenvironments having significantly different pH values.

An example of one type of osmotic device comprises two component layers within a compartment (herein referred to as, and used interchangeably with, a core) formed by a semipermeable wall. One component layer (herein referred to as an active layer) comprises drug (i.e. deutetrabenazine) in a mixture with an excipient(s) and the second component layer (herein referred to as a push layer) comprises an osmotically active agent(s), optionally in a mixture with excipients but does not contain drug. This core is further coated by the semipermeable wall, which permits entry of aqueous fluid, i.e. from the GI system, into the core. Without wishing to be limited to theory, as fluid is imbibed into the dosage form, the active layer forms a drug formulation and the osmotic agent(s) in the push layer swell and push against the drug formulation to thereby facilitate release of the drug formulation at a substantially constant rate. See, e.g., U.S. Pat. Nos. 4,327,725; 4,612,008; 4,783,337; and 5,082,668.

Although constant-release dosage forms have been proven effective for many different drug therapies, there are clinical situations where these have not been entirely satisfactory. It has been observed that for some patients, the therapeutic effectiveness of the drug decreases below the therapeutically effective threshold before the end of the desired therapy period despite the maintenance of substantially constant drug release that would be expected to provide continued effectiveness.

It has been surprisingly discovered that oral dosage forms comprising deutetrabenazine that exhibit a desirable rate of release and hence a desirable pharmacokinetic profile for an extended time can be achieved. In some embodiments, the presently disclosed osmotic dosage forms provide a pharmacokinetic profile when administered orally to a subject on a once daily basis (q.d.) that is comparable, e.g., bioequivalent, to that of the AUSTEDO® dosage forms administered b.i.d. In certain embodiments, the osmotic dosage forms provide an in vivo plasma profile for total deuHTBZ at steady state that includes a mean $AUC_{0-24}$ of about 410,000 to 800,000 h*pg/mL, and a mean $C_{max}$ of less than about 40,000 pg/mL.

The osmotic dosage forms of the present disclosure include a tablet core containing at least a push layer and an active layer, wherein the active layer includes deutetrabenazine and one or more excipient for forming a drug formulation when hydrated, and wherein the push layer includes at least one osmotic agent and one or more excipient. Both the push layer and active layer are contained within a tablet core at least partially surrounded by a semipermeable layer having a port that functions as an exit means for drug formulation release from the tablet core. In some embodiments, the two layers are compressed into a bilayer tablet core surrounded by a semipermeable membrane and further having a suitable orifice for drug release there through.

An embodiment of an oral osmotic dosage form disclosed herein is illustrated in the cross section in FIG. 1. The components are not drawn to scale. The dosage form (2) comprises a bilayer tablet core. The core comprises an active layer (4), containing drug, e.g. deutetrabenazine, and one or more active layer excipients, and a push layer (6), containing at least one osmotic agent along with one or more push layer excipients. At least a portion of the active layer forms a drug formulation upon exposure to an aqueous milieu. Suitable active layer and push layer excipients are known in the art and include diluents, carriers, binders, fillers, control release agents and processing aids. A semipermeable membrane (8) surrounds the bilayer tablet core and a suitably sized port (10) that extends from the semipermeable membrane into the active layer (4) is present to permit drug formulation to be released from within the tablet core. As illustrated, the dosage form may be longitudinally compressed and the port (10) present on the side of the dosage form comprising the active layer. In other embodiments, the dosage form is compressed along the lateral axis of the dosage form, and the port is present on one end of the dosage form. In all embodiments, more than one port may be present. Through cooperation of the osmotic dosage form components and in the presence of an aqueous milieu, drug formulation is released from the active layer through the port at a desired release rate for an extended time. Although not shown in FIG. 1, an optional immediate-release layer (immediate release coating), external to the semipermeable layer, including further drug (ie deutetrabenazine microparticles) may be further provided, if desired, as described elsewhere herein.

In one embodiment, the invention provides an osmotic dosage form for once daily administration to a subject in need thereof comprising:

a. a tablet core comprising an active layer comprising an amount of deutetrabenazine microparticles and a push layer;

b. a semipermeable layer surrounding the tablet core; and c. a port in the semipermeable layer extending to the tablet core.

The active layer contained within the tablet core includes deutetrabenazine and pharmaceutically acceptable active layer excipients. In preferred embodiments, the deutetrabenazine is provided as deutetrabenazine microparticles. The deutetrabenazine microparticles may be present in the active layer in an amount of about 2% to 20% (i.e., about 2%, 3%, 4%, 5%, 6%, 7%, 8%, 9%, 10%, 11%, 12%, 13%, 14%, 15%, 16%, 17%, 18%, 19%, 20%), by weight (% w/% w) based on the total weight of the active layer.

In a specific embodiment, the active layer excipient comprises an active layer control release agent. In an embodiment of the invention, the active layer control release agent has a viscosity of about 50-150 mPa s. In one specific embodiment, the active layer control release agent has a viscosity of about 55-90 mPa s. In a preferred embodiment, the active layer control release agent comprises a polyoxyethylene polymer, an ionic hydrogel, a hydrophilic polymer, a hydrophobic polymer or any mixture thereof. In another embodiment, the active layer control release agent comprises a polyoxyethylene polymer, which is polyethylene oxide. In yet another embodiment, the polyethylene oxide within the active layer has an average molecular weight of 100,000 daltons to 500,000 daltons. In some embodiments, the polyethylene oxide within the active layer has an average molecular weight of about 200,000 daltons.

In another embodiment, the active layer control release agent is present in the active layer in an amount of about 60% to about 98% by weight, based on the total weight of the active layer. In one specific embodiment, the active layer control release agent is present in the active layer in an amount of about 70% to about 85% by weight, based on the total weight of the active layer. In one specific embodiment, the active layer control release agent is present in the active layer in an amount of about 80% to about 90% by weight, based on the total weight of the active layer. In one specific embodiment, the active layer control release agent is present in the active layer in an amount of about 85% to about 95% by weight, based on the total weight of the active layer.

In one embodiment, the weight ratio of the amount of deutetrabenazine microparticles and the amount of active layer control release agent in the active layer is 2:3-1:50. In one specific embodiment, the weight ratio of the amount of deutetrabenazine microparticles and the amount of active layer control release agent in the active layer is 2:5-1:5. In one specific embodiment, the weight ratio of the amount of deutetrabenazine microparticles and the amount of active layer control release agent in the active layer is 1:4-1:9. In one specific embodiment, the weight ratio of the amount of deutetrabenazine microparticles and the amount of active layer control release agent in the active layer is 1:5-1:19. In one specific embodiment, the weight ratio of the amount of deutetrabenazine microparticles and the amount of active layer control release agent in the active layer is 1:5-1:10. In one specific embodiment, the weight ratio of the amount of deutetrabenazine microparticles and the amount of active layer control release agent in the active layer is 1:5-1:7. In one specific embodiment, the weight ratio of the amount of deutetrabenazine microparticles and the amount of active layer control release agent in the active layer is 1:12-1:15. In one specific embodiment, the weight ratio of the amount of deutetrabenazine microparticles and the amount of active layer control release agent in the active layer is 1:20-1:30.

Optional excipients within the active layer include antioxidants, binders, lubricants, colorants, and the like. Such excipients are well known among those of ordinary skill in the art. In some embodiments the active layer comprises deutetrabenazine microparticles, an active layer excipient and optionally one or more of an antioxidant, a binder, a lubricant, a colorant, or any combination thereof.

In one embodiment, the active layer further comprises at least one active layer antioxidant. Preferably, the active layer antioxidant comprises: tertiary butyl-4-methoxyphenol (mixture of 2 and 3-isomers), 2,6-ditertiary butyl-p-cresol, propyl gallate, 6-ethoxy-1,2-digydro-2,2,4-trimethylquinoline (ethoxyquin), nordihydroguaiaretic acid (NDGA), butylated hydroxyanisole, butylated hydroxytoluene or any mixture thereof. In one specific embodiment, the active layer comprises a mixture of butylated hydroxyanisole and butylated hydroxytoluene. In one embodiment, the active layer antioxidant may be present in the active layer in an amount of about 0.001% to about 1% by weight, based on the total weight of the active layer.

In one embodiment, the active layer further comprises an active layer binder. In an embodiment, the active layer binder comprises hypromellose (hydroxypropyl methylcellulose), starch, gelatin, agar, natural and synthetic gums and any mixture thereof. In another embodiment, the active layer binder comprises hypromellose. In one embodiment, the active layer binder may be present in the active layer in an amount of about 2% to about 20% by weight, based on the total weight of the active layer.

In one embodiment, the active layer further comprises one or more pharmaceutically acceptable lubricant. Suitable lubricants include, without limitation, talc, starch, zinc stearate, aluminum stearate, magnesium stearate, calcium stearate, boric acid, sodium chloride, paraffin, stearic acid, low melting point waxes, hydrogenated vegetable oils and saturated fatty acid esters. In a specific embodiment, one or more lubricants may be present in the active layer in an amount of about 0.001% to about 0.2% by weight, based on the total weight of the active layer.

In an embodiment, the active layer comprises deutetrabenazine microparticles, and an active layer control release agent having a viscosity of about 55-90 mPa s. In some embodiments, the active layer control release agent comprises polyethylene oxide. In yet another embodiment, the active layer comprises deutetrabenazine microparticles, polyethylene oxide and further comprises butylated hydroxyanisole, butylated hydroxytoluene, hypromellose and magnesium stearate.

The push layer contained within the tablet core comprises an osmotic agent which, without being bound to theory, acts as a fluid-attracting agent which swells when exposed to an aqueous milieu and pushes against the active layer enabling the flow of the drug formulation from within the dosage form out into an external environment. The osmotic agent, is defined as, for example, a non-volatile species which is generally soluble in water and create the osmotic gradient thereby enabling the osmotic inflow of water. Species which fall within the category of osmotic agent include inorganic salts or carbohydrates. Non limiting examples of osmotic agents are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any one of these various species.

In one embodiment, the osmotic agent is present in the push layer in an amount of about 5% to about 50% by weight, based on the total weight of the dosage form. In an embodiment, the osmotic agent is present in the push layer in an amount of about 5% to about 20% by weight, based on the total weight of the dosage form. In another embodiment, the osmotic agent is present in the push layer in an amount of about 8% to about 10% by weight, based on the total weight of the dosage form.

In one embodiment, the osmotic agent is present in the push layer in an amount of about 20% to about 40% by weight, based on the total weight of the push layer. In an embodiment, the osmotic agent is about 30% by weight, based on the total weight of the push layer.

The push layer further comprises one or more excipients, such as a control release agent. In one embodiment, the push layer comprises an osmotic agent and a push layer control release agent. Push layer control release agents include polymers providing a swellable matrix upon contact with water. In one embodiment, the push layer control release agent has a viscosity of about 5500-7500 mPa s.

Examples of a push layer control release agent include polyoxyethylene polymers, ionic hydrogels, hydrophilic polymers, hydrophobic polymers and any mixture thereof. In one embodiment, the push layer control release agent comprises a polyoxyethylene polymer, which is polyethylene oxide. In another embodiment, the polyethylene oxide within the push layer has an average molecular weight of 1,000,000 daltons to 7,000,000 daltons. In yet another embodiment, the polyethylene oxide within the push layer has an average molecular weight of 5,000,000 daltons.

In one embodiment, the push layer control release agent is present in the push layer in an amount of about 50% to about 80% by weight, based on the total weight of the push layer. In another embodiment, the push layer control release agent is present in the push layer in an amount of about 60% to about 70% by weight, based on the total weight of the push layer.

In one embodiment, the weight ratio of the osmotic agent and the push layer control release agent in the push layer is 1:2-1:3.5 or about 1:2 to 1:2.5.

The push layer optionally further contains other pharmaceutically acceptable excipients, e.g., for stabilizing the layer, providing color for tablet orientation, or the like. Exemplary excipients include binders, colorants, and lubricants, and suitable examples of these types of excipients are well known among those of ordinary skill in the art.

In one embodiment, the push layer further comprises a push layer binder. The push layer binder can be selected from hypromellose (hydroxypropyl methylcellulose), starch, gelatin, agar, natural and synthetic gums, and any mixture thereof. Preferably, the push layer binder is hypromellose. In one embodiment, the push layer binder is present in the push layer in an amount of about 2% to about 10% by weight, based on the total weight of the push layer. In another embodiment, the push layer binder is present in the push layer in an amount of about 3% to about 6% by weight, based on the total weight of the push layer.

Lubricants within the push layer can include any of the exemplary materials described supra in connection with the active layer. The push layer may also include a disintegrant such as cross-linked polyvinylpyrrolidone, corn starch, potato starch, smectite clay (e.g magnesium aluminum silicate such as Veegum®), bentonite and citrus pulp. It may also be desirable to include stabilizers for the drug. These include, without limitation, sodium bisulfate and histidine HCl.

In one specific embodiment, the push layer comprises sodium chloride, polyethylene oxide, hydroxypropyl methylcellulose, a colorant, and magnesium stearate.

The present osmotic dosage forms include a semipermeable layer that surrounds the tablet core, thereby enabling influx of fluid from an external fluid environment (e.g., a subject's gastrointestinal tract) into the tablet core while preventing efflux of drug from the core. The semipermeable layer is preferably formed of a material that does not adversely affect the patient, and is permeable to an external fluid such as water and biological fluids. The selectively permeable materials forming the semipermeable layer are insoluble in body fluids, and are non-erodible or are bioerodible after a predetermined period with bioerosion corresponding to the end of the drug formulation release period. As used herein, "semipermeable layer", "semipermeable wall" and "semipermeable membrane" are interchangeable.

Generally, semipermeable materials useful for forming the semipermeable layer may have a fluid permeability of $10^{-5}$ to $10^{-1}$ (cc mil/cm$^2$ hr atm) expressed per atmosphere of hydrostatic or osmotic pressure difference across the wall at the temperature of use. Suitable materials are known in the art, see, e.g., U.S. Pat. Nos. 3,845,770 and 3,916,899.

Typical materials useful for forming the semipermeable layer include materials known in the art including cellulose acetate, cellulose triacetate, agar acetate, amylose triacetate, beta glucan acetate, cellulose diacetate, acetaldehyde dimethyl acetate, cellulose acetate ethyl carbamate, polyamides, polyurethane, sulfonated polystyrenes, cellulose acetate phthalate, cellulose acetate methyl carbamate, cellulose acetate succinate, cellulose acetate dimethylaminoacetate, cellulose acetate ethyl carbamate, cellulose acetate chloroacetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, selectively permeable polymers formed by the coprecipitation of a polycation and a polyanion as disclosed in U.S. Pat. Nos. 3,173,876; 3,276,586; 3,541,005; 3,541,006; and 3,546,142.

In one embodiment, the semipermeable layer comprises water soluble polymers or water insoluble polymers including cellulose acetate, cellulose diacetate, cellulose triacetate, cellulose propionate, cellulose acetate butyrate; cellulose ethers including ethyl cellulose, agar acetate, amylose triacetate, betaglucan acetate, poly(vinyl methyl) ether copolymers, poly(orthoesters), poly acetals and selectively permeable poly(glycolic acid), poly(lactic acid) derivatives and any mixture thereof. Cellulose acetate includes cellulose acetate polymers (e.g. Eudragit®). In one embodiment, the semipermeable layer comprises a water insoluble polymer, which is present in an amount of about 80% to about 99.9% by weight, based on the weight of the semipermeable layer. In another embodiment, the water insoluble polymer is about 85% to about 95% by weight, based on the weight of the semipermeable layer. Preferably, the semipermeable layer comprises a water insoluble polymer which is cellulose acetate, comprising about 32%-40% acetyl content.

The semipermeable layer may further include a pore-forming agent or "pore former". Pore forming agents include biocompatible materials that when contacted with body fluids dissolve, disperse or degrade to create pores or channels in the semipermeable layer material. Typically, water soluble organic and non-organic materials such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropylcellulose, and the like) can conveniently be used as pore formers. In one embodiment, the semipermeable layer comprises, in addition to the water soluble polymer or water insoluble polymer, a pore-forming agent, which is selected from water soluble sugars, water soluble salts, water soluble solvents and water soluble polymers or any mixture thereof. In a specific embodiment, the pore-forming agent is a water soluble solvent, which is polyethylene glycol. In one embodiment, the pore-forming agent comprises about 0.1% to about 20% by weight of the semipermeable layer. Preferably, the pore-forming agent comprises about 8% to about 15% by weight of the semipermeable layer. In one embodiment, the weight ratio of the semipermeable layer and the tablet core is 1:8-1:10.

In one specific embodiment, the semipermeable layer comprises cellulose acetate and polyethylene glycol.

The present dosage forms include a port(s), independently of or in addition to the pore-forming agent. The port is present within the semipermeable layer and extends from external to the semipermeable layer into the tablet core providing an exit means for the drug formulation from the active layer within the tablet core into the environment external to the dosage form. The exit port(s) are formed by any means known in the art including mechanical drilling, laser drilling, eroding an erodible element, extracting, dissolving, bursting, or by leaching. For example, the port(s) may be formed by post-coating mechanical or thermal means or with a beam of light (e.g., a laser), a beam of particles, or other high-energy source, or may be formed in situ by rupture of a small portion of the coating. Such rupture may be controlled by intentionally incorporating a relatively small weak portion into the coating. Exit port(s) may also be formed in situ by erosion of a plug of water-soluble material or by rupture of a thinner portion of the coating over an indentation in the core. Exit port(s) may be formed by coating the core such that one or more small regions remains uncoated. In addition, the exit port(s) can be a large number of holes or pores that may be formed during coating. The exit port(s) can be a pore formed by leaching sorbitol, lactose or the like from a wall or layer as disclosed in U.S. Pat. No. 4,200,098. This patent discloses pores of controlled-size porosity formed by dissolving, extracting, or leaching a material from a wall, such as sorbitol from cellulose acetate. A preferred form of laser drilling is the use of a pulsed laser that incrementally removes material from the semipermeable layer to the desired depth to form the exit port. In certain embodiments, a port, or a plurality of ports, can be formed, for example, by leaching a member selected from the group consisting of sorbitol, lactose, fructose, glucose, mannose, galactose, talose, sodium chloride, potassium chloride, sodium citrate and mannitol to provide a uniform-release dimensioned exit port. The exit means can have any shape, such as round, triangular, square, elliptical and the like for the uniform metered dose release of a drug formulation from the dosage form. The osmotic dosage form can be constructed with one or more exits ports in spaced-apart relation or one or more surfaces of the osmotic dosage form. Such exits and equipment for forming such exits are disclosed, for example, in U.S. Pat. Nos. 3,916,899 and 4,088,864.

In one embodiment, the port has a diameter of from about 0.1 mm to about 1 mm. In another embodiment, the port has a diameter of from about 0.4 mm to about 0.8 mm.

In some embodiments, the dosage form further includes one or more seal coatings for example, in order to ensure integrity of one or more subparts of the present dosage forms. In one embodiment, the tablet core comprises a seal coating immediately external to the tablet core. For example, a tablet core seal coating may be applied to the outer surface of the compressed, layered tablet core prior to application of the semipermeable layer. In certain embodiments, the tablet core comprises a semipermeable layer immediately external to the tablet core and a seal coating immediately external to the semipermeable layer. For example, a semipermeable layer seal coating may be applied to the outer surface of the dosage form following application of the semipermeable membrane to the tablet core. Seal coating materials can include binders, numerous types of which are disclosed supra. In embodiments comprising seal coating between the core and immediately external to the semipermeable membrane, the port will extend from external to the seal coating through all layers and into the core.

In one embodiment, a tablet core seal coat is applied to the outer surface of the tablet core.

In one embodiment, a semipermeable layer seal coat applied to the outer surface of the semipermeable layer.

In one embodiment, the tablet core seal coat and or the semipermeable layer seal coat comprises a binder which can be selected from: hypromellose (hydroxypropyl methylcellulose), starch, gelatin, agar, natural and synthetic gums and any mixture thereof. In another embodiment, the tablet core seal coat binder and or the semipermeable layer seal coat binder is hypromellose.

In one embodiment, the total amount of the binder within the dosage form is from about 0 to about 20% by weight, based on the total weight of the dosage form. In another embodiment, the total amount of the binder within the dosage form is form about 5% to about 20% by weight, based on the total weight of the dosage form. In yet another embodiment, the total amount of the binder within the dosage form is about 8% to about 10% by weight, based on the total weight of the dosage form or about 10% to about 20% by weight, based on the total weight of the dosage form.

The absolute amount of deutetrabenazine in the active layer of the present osmotic dosage forms will depend on the dosage strength of the particular embodiment. As described more fully below, the dosage forms may further include an immediate release amount of deutetrabenazine microparticles that is external to the active layer, preferably external to the semipermeable membrane layer.

In one embodiment, the dosage forms disclosed herein further comprise an immediate release coating comprising a second amount of deutetrabenazine microparticles, external to the semipermeable membrane or external to the semipermeable layer seal coating applied thereto.

In one embodiment, the immediate release coating comprises about 0.1% to about 25% by weight deutetrabenazine microparticles, based on the total weight of the dosage form. In another embodiment, the immediate release coating comprises about 0.2% to about 5% by weight deutetrabenazine microparticles, based on the total weight of the dosage form. In another embodiment, the immediate release coating comprises about 0.3% to about 2% by weight deutetrabenazine microparticles, based on the total weight of the dosage form In another embodiment, wherein the dosage form comprises a total of 24 mg of deutetrabenazine microparticles, the immediate release coating comprises about 1% to about 2% by weight deutetrabenazine microparticles, based on the total weight of the dosage form. In another embodiment, wherein the dosage form comprises a total of 12 mg of deutetrabenazine microparticles, the immediate release coating comprises about 0.5% to about 1% by weight deutetrabenazine microparticles, based on the total weight of the dosage form. In yet another embodiment, wherein the dosage form comprises a total of 6 mg of deutetrabenazine microparticles, the immediate release coating comprises about 0.1% to about 0.5% by weight deutetrabenazine microparticles, based on the total weight of the dosage form.

In one embodiment, at least 70% of the total amount of deutetrabenazine microparticles in the dosage form is present within the active layer. In another embodiment, 70% to 100% of the total amount of deutetrabenazine microparticles in the dosage form, is present within the active layer. In yet another embodiment, about 70% to 80% of the total amount of deutetrabenazine microparticles in the present dosage forms is present within the active layer. In some embodiments of the osmotic dosage forms, deutetrabenazine is present solely in the active layer.

In the embodiments in which the osmotic dosage forms comprise an immediate release coating, comprising up to about 30% of the total amount of deutetrabenazine microparticles in the dosage form. In one embodiment, about 8% to 30% of the total amount of deutetrabenazine microparticles in the dosage form is present within an immediate release coating. In one embodiment of the invention, about 70% to about 80% of the total amount of deutetrabenazine microparticles in the present dosage forms is present within the active layer and about 20% to about 30% of the total amount of deutetrabenazine microparticles in the dosage form, is present within an immediate release coating.

The dosage form of any embodiment of the invention comprises a total amount of deutetrabenazine microparticles of from about 6 mg to about 48 mg. In one embodiment, the total amount of deutetrabenazine microparticles in the dosage form is about 6 mg. In one embodiment, the total amount of deutetrabenazine microparticles in the dosage form is about 12 mg. In another embodiment, the total amount of deutetrabenazine microparticles in the dosage form is about 24 mg. In yet another embodiment, the total amount of deutetrabenazine microparticles in the dosage form is about 36 mg. Yet in another embodiment, the total amount of deutetrabenazine microparticles in the dosage form is about 48 mg.

According to the disclosure, the total amount of deutetrabenazine or the total daily dose of deutetrabenazine, used herein interchangeably, is administered to a subject as a one dose a day (QD). Depending on the total daily dose, one or more than one (multiple) dosage forms may be administered to a subject at one dose. Preferably, a single dosage form is administered at one dose. In one embodiment, the total daily dose of deutetrabenazine is from 12 mg to 48 mg. In one embodiment, the total daily dose of deutetrabenazine is 12 mg. In one embodiment, the total daily dose of deutetrabenazine is 18 mg. In one embodiment, the total daily dose of deutetrabenazine is 24 mg. In one embodiment, the total daily dose of deutetrabenazine is 30 mg. In one embodiment, the total daily dose of deutetrabenazine is 36 mg. In one embodiment, the total daily dose of deutetrabenazine is 42 mg. In one embodiment, the total daily dose of deutetrabenazine is 48 mg.

Patients being treated with deutetrabenazine twice daily (bid) may be switched to deutetrabenazine once daily (qd), at the same total daily dose, the day following a last dose of deutetrabenazine bid.

Patients being treated with deutetrabenazine once daily (qd) may be switched to deutetrabenazine twice daily (bid), at the same total daily dose, the day following a last dose of deutetrabenazine qd.

Patients being treated with tetrabenazine may be switched to deutetrabenazine once daily osmotic dosage form disclosed herein (qd), the day following a last dose of tetrabenazine.

In one embodiment, the total amount of deutetrabenazine microparticles present within the dosage form is about 0.5% to about 15% by weight, based on the total weight of the osmotic dosage form. In another embodiment, the total amount of deutetrabenazine microparticles present within the dosage form is about 1% to about 10% by weight, based on the total weight of the dosage form. In another embodiment, wherein the dosage form comprises a total of 6 mg of deutetrabenazine microparticles, the total amount of deutetrabenazine microparticles present within the dosage form is about 0.5% to about 3% by weight, based on the total weight of the dosage form. In another embodiment, wherein the dosage form comprises a total of 12 mg of deutetrabenazine microparticles, the total amount of deutetrabenazine microparticles present within the dosage form is about 1% to about 5% by weight, based on the total weight of the dosage form. In another embodiment, wherein the dosage form comprises a total of 24 mg of deutetrabenazine microparticles, the total amount of deutetrabenazine microparticles present within the dosage form is about 5% to about 10% by weight, based on the total weight of the dosage form.

In addition to an amount of deutetrabenazine microparticles, the immediate release coating may further include one or more pharmaceutically acceptable excipients such as an antioxidant, a binder, and a surfactant or any combination thereof. Antioxidants, binders, and surfactants may be selected from a wide variety of choices known among those skilled in the art. Exemplary antioxidants and binders are disclosed supra in connection with the other components of the present dosage forms. Surfactants may include, but are not limited to, esters of polyhydric alcohols such as glycerol monolaurate, ethoxylated castor oil, polysorbates, esters or ethers of saturated alcohols such as myristyl lactate (e.g. Ceraphyl®50), and polyoxyethylene/polyoxypropylene block copolymers, such as Pluronic®.

In one embodiment, the immediate release coating further comprises an antioxidant which can be selected from: tertiary butyl-4-methoxyphenol (mixture of 2 and 3-isomers), 2,6-ditertiary butyl-p-cresol, propyl gallate, 6-ethoxy-1,2-digydro-2,2,4-trimethylquinoline (ethoxyquin), nordihydroguaiaretic acid (NDGA), butylated hydroxyanisole, butylated hydroxytoluene and any mixture thereof. In another embodiment, the immediate release coating comprises a mixture of butylated hydroxyanisole, and butylated hydroxytoluene. In another embodiment, the immediate release coating comprises deutetrabenazine microparticles, butylated hydroxyanisole, butylated hydroxytoluene, hypromellose and polysorbate 80.

In one embodiment, provided is an osmotic dosage form for once daily administration of deutetrabenazine to a subject in need thereof comprising:
  a. a tablet core comprising:
    i. an active layer comprising an amount of deutetrabenazine microparticles and an active layer control release agent comprising a polymer having a viscosity of about 55-90 mPa s, an active layer antioxidant, an active layer binder;
    ii. a push layer comprising an osmotic agent and a push layer control release agent comprising a polymer having a viscosity of about 5500-7500 mPa s and a push layer binder;
  b. a tablet core seal coat comprising a binder on the outer surface of the tablet core;
  c. a semipermeable layer comprising a water insoluble polymer and a pore-forming agent surrounding the tablet core seal coat;
  d. a semipermeable layer seal coat comprising a binder on the outer surface of the semipermeable layer;
  e. an immediate release coating comprising a second amount of deutetrabenazine microparticles and an immediate release coating antioxidant on the outer surface of the semipermeable layer seal coat; and
  f. a port in the semipermeable layer seal coat reaching the tablet core.

In some embodiments, provided is an osmotic dosage form according to any one of the embodiments of the invention, wherein not more than 15% of the drug formulation is released within 2 hours and/or wherein not more than 60% of the drug formulation is released within 8 hours, when the dosage form is tested in 500 mL acid phosphate buffer at pH 3.0 using a USP II dissolution apparatus.

Further provided, herein is a method of treating a hyperkinetic movement disorder in a subject comprising orally administering, on a once daily basis to the subject, an osmotic dosage form according to any one of the embodiments of the invention. Further provided is an osmotic dosage form according to any one of the embodiments disclosed herein for oral once a day use in treating a hyperkinetic movement disorder in a subject.

In some embodiments, the movement disorder is selected from chorea, akathisia, dyskinesia, tremor, or tic. In some embodiments, the movement disorder is selected from chorea associated with Huntington's disease, tardive dyskinesia, a tic associated with Tourette syndrome, Parkinson's disease levodopa-induced dyskinesia or dyskinesia in cerebral palsy.

In certain embodiments, the osmotic dosage form according to any one of the embodiments disclosed herein, is administered with food.

In certain embodiments, the osmotic dosage form according to any one of the embodiments disclosed herein, is administered under fasting conditions.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 6 mg of deutetrabenazine microparticles, provides an in vivo plasma profile for total α- and β-dihydrodeutetrabenazine that includes a geometric mean $AUC_{0-inf}$ of about 91,250 to 142,750 h*pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 6 mg of deutetrabenazine microparticles, provides an in vivo plasma profile for total α- and β-dihydrodeutetrabenazine that includes a geometric mean $C_{max}$ of less than about 4,600 pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 12 mg of deutetrabenazine microparticles, provides an in vivo plasma profile for total α- and β-dihydrodeutetrabenazine that includes a geometric mean $AUC_{0-inf}$ of about 182,500 to 285,500 h*pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 12 mg of deutetrabenazine microparticles, provides an in vivo plasma profile for total α- and β-dihydrodeutetrabenazine that includes a geometric mean $C_{max}$ of less than about 9,200 pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 24 mg of deutetrabenazine microparticles, provides an in vivo plasma profile for total α- and β-dihydrodeutetrabenazine that includes a geometric mean $AUC_{0-inf}$ of about 365,000 to 571,000 h*pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 24 mg of deutetrabenazine microparticles, provides an in vivo plasma profile for total α- and β-dihydrodeutetrabenazine that includes a geometric mean $C_{max}$ of less than about 18,400 pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 36 mg of deutetrabenazine microparticles, provides an in vivo plasma profile for total α- and β-dihydrodeutetrabenazine that includes a geometric mean $AUC_{0-inf}$ of about 547,500 to 856,500 h*pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 36 mg of deutetrabenazine microparticles, provides an in vivo plasma profile for total α- and β-dihydrodeutetrabenazine that includes a geometric mean $C_{max}$ of less than about 27,600 pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 48 mg of deutetrabenazine microparticles, provides an in vivo plasma profile for total α- and β-dihydrodeutetrabenazine that includes a geometric mean $AUC_{0-inf}$ of about 730,000 to 1,142,000 h*pg/mL.

In one embodiment, the invention provides a method of treating a hyperkinetic movement disorder in a subject in need thereof comprising orally administering to the subject a once daily osmotic dosage form according to any one of the embodiments of the invention wherein single dose administration of the osmotic dosage form, which comprises a total amount of 48 mg of deutetrabenazine microparticles, provides an in vivo plasma profile for total α- and β-dihydrodeutetrabenazine that includes a geometric mean $C_{max}$ of less than about 36,800 pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 6 mg of deutetrabenazine microparticles provides an in vivo plasma profile for total α- and β-dihydrodeutetrabenazine at steady state that includes a mean $AUC_{0-24}$ of about 102,500 to 200,000 h*pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 6 mg of deutetrabenazine microparticles, provides an in vivo plasma profile for total α- and β-dihydrodeutetrabenazine at steady state that includes a mean $C_{max}$ of less than about 10,000 pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 12 mg of deutetrabenazine microparticles, provides an in vivo plasma profile for total α- and β-dihydrodeutetrabenazine at steady state that includes a mean $AUC_{0-24}$ of about 205,000 to 400,000 h*pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 12 mg of deutetrabenazine microparticles, provides an in vivo plasma profile for total α- and β-dihydrodeutetrabenazine at steady state that includes a mean $C_{max}$ of less than about 20,000 pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 24 mg of deutetrabenazine microparticles, provides an in vivo plasma profile for total α- and β-dihydrodeutetrabenazine at steady state that includes a mean $AU_{0-24}$ of about 410,000 to 800,000 h*pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 24 mg of deutetrabenazine microparticles, provides an in vivo plasma profile for total $\alpha$- and $\beta$-dihydrodeutetrabenazine at steady state that includes a mean $C_{max}$ of less than about 40,000 pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 36 mg of deutetrabenazine microparticles, provides an in vivo plasma profile for total $\alpha$- and $\beta$-dihydrodeutetrabenazine at steady state that includes a mean $AUC_{0-24}$ of about 615,000 to 1,200,000 h*pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 36 mg of deutetrabenazine microparticles, provides an in vivo plasma profile for total $\alpha$- and $\beta$-dihydrodeutetrabenazine at steady state that includes a mean $C_{max}$ of less than about 60,000 pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 48 mg of deutetrabenazine microparticles, provides an in vivo plasma profile for total $\alpha$- and $\beta$-dihydrodeutetrabenazine at steady state that includes a mean $AUC_{0-24}$ of about 820,000 to 1,600,000 h*pg/mL.

In one embodiment, the invention provides a method of treating a hyperkinetic movement disorder in a subject in need thereof comprising orally administering to the subject a once daily osmotic dosage form according to any one of the embodiments of the invention wherein the osmotic dosage form which comprises a total amount of 48 mg of deutetrabenazine microparticles, provides an in vivo plasma profile for total $\alpha$- and $\beta$-dihydrodeutetrabenazine at steady state that includes a mean $C_{max}$ of less than about 80,000 pg/mL.

In one embodiment, the invention provides a method of treating a hyperkinetic movement disorder comprising: administering an osmotic dosage form according to any one of the embodiments of the invention, wherein not more than 15% of the drug formulation is released after 2 hours when tested in 500 mL acid phosphate buffer at pH 3.0 using a USP II dissolution apparatus.

In one embodiment, the invention provides a method of treating a hyperkinetic movement disorder in a subject in need thereof comprising: administering to the subject a once daily osmotic dosage form according to any one of the embodiments of the invention, wherein not more than 60% of the drug formulation is released within 8 hours when tested in 500 mL acid phosphate buffer at pH 3.0 using a USP II dissolution apparatus.

In some embodiments, the invention provides a method of treating a hyperkinetic movement disorder comprising: administering an osmotic dosage form according to any one of the embodiments of the invention, wherein not more than 15% of the drug formulation is released after 2 hours and wherein not more than 60% of the drug formulation is released within 8 hours when tested in 500 mL acid phosphate buffer at pH 3.0 using a USP II dissolution apparatus.

Further provided is a method of transitioning a human subject being treated with a total daily dose of deutetrabenazine twice daily (bid) to the total daily dose of deutetrabenazine once daily for control of abnormal involuntary movement, comprising:

a) administering to the human subject a last dose of the deutetrabenazine twice daily (bid); and b) the next day, administering to the human subject the total daily dose of deutetrabenazine once daily (qd).

The deutetrabenazine once daily is, for example, a deutetrabenazine extended release osmotic dosage form disclosed herein.

Deutetrabenazine twice daily may refer to, for example, AUSTEDO® bid tablets or any equivalent thereof. As used herein, the term "last dose" refers to discontinuation of current treatment, for example, discontinuing treatment with deutetrabenazine twice daily. In specific embodiments, last dose of the deutetrabenazine twice daily may refer to the second daily dose of deutetrabenazine twice daily, administered to the human subject, for example, in the afternoon or evening.

In one embodiment, the human subject is being treated with deutetrabenazine twice daily tablets at a total daily dose of 12 mg, and is transitioned to a total daily dose of 12 mg deutetrabenazine once daily.

In another embodiment, the human subject is being treated with deutetrabenazine twice daily tablets at a total daily dose of 18 mg, and is transitioned to a total daily dose of 18 mg deutetrabenazine once daily.

In another embodiment, the human subject is being treated with deutetrabenazine twice daily tablets at a total daily dose of 24 mg, and is transitioned to a total daily dose of 24 mg deutetrabenazine once daily.

In another embodiment, the human subject is being treated deutetrabenazine twice daily tablets at a total daily dose of 30 mg, and is transitioned to a total daily dose of 30 mg deutetrabenazine once daily.

In another embodiment, the human subject is being treated with deutetrabenazine twice daily tablets at a total daily dose of 36 mg, and is transitioned to a total daily dose of 36 mg deutetrabenazine once daily.

In another embodiment, the human subject is being treated with deutetrabenazine twice daily tablets at a total daily dose of 42 mg, and is transitioned to a total daily dose of 42 mg deutetrabenazine once daily.

In another embodiment, the human subject is being treated with deutetrabenazine twice daily tablets at a total daily dose of 48 mg, and is transitioned to a total daily dose of 48 mg deutetrabenazine once daily.

In one specific embodiment, the deutetrabenazine once daily is an extended-release osmotic dosage form, preferably, a deutetrabenazine osmotic dosage form according to any one of the embodiments of the invention.

In yet another specific embodiment, the deutetrabenazine once daily osmotic dosage form comprises:

a. a tablet core comprising an active layer and a push layer, wherein the active layer comprises an amount of deutetrabenazine microparticles and an active layer control release agent, and wherein the push layer comprises an osmotic agent and a push layer control release agent, and an optional tablet seal coat on the outer surface of the tablet core, wherein about 70%-80% of the total amount of deutetrabenazine microparticles present in the dosage form is present within the active layer and wherein about 20%-30% of the total amount of deutetrabenazine microparticles present in the dosage form, is present within the immediate release coating and wherein the deutetrabenazine microparticles have a particle size with $D_{90}$ of 15 µm, a $D_{50}$ 10 µm, and/or a $D_{10}$ of 3 µm;

b. a semipermeable layer surrounding the tablet core;

c. a port extending through the semipermeable layer into the tablet core; and d. an optional immediate release coating external to the semipermeable layer comprising a second amount of deutetrabenazine microparticles.

In one embodiment, the deutetrabenazine once daily extended-release dosage form is administered with food or without food.

In one embodiment, the abnormal involuntary movement being controlled during the transition from the deutetrabenazine twice daily to the deutetrabenazine once daily dose is chorea, akathisia, dyskinesia, tremor, tic, chorea associated with Huntington's disease, tardive dyskinesia, a tic associated with Tourette syndrome, Parkinson's disease levodopa-induced dyskinesia or dyskinesia in cerebral palsy. In one embodiment, the abnormal involuntary movement being controlled is chorea associated with Huntington's disease. In one embodiment, the abnormal involuntary movement being controlled is tardive dyskinesia.

Further provided is a method of transitioning a human subject being treated with a total daily dose of deutetrabenazine once daily to deutetrabenazine twice daily (bid) tablets at the same total daily dose, for control of abnormal involuntary movement, comprising:

a) administering a last dose of the deutetrabenazine once daily; and b) the next day, administering to the human subject the total daily dose of deutetrabenazine twice daily.

As detailed above, a human subject is transitioned to the same total daily dose, for example, 12 mg, 18 mg, 24 mg, 30 mg, 36 mg, 42 mg or 48 mg.

In one embodiment, the human subject is being treated with a dose of a deutetrabenazine once daily at a total daily dose of 12 mg, and is transitioned to a total daily dose of 12 mg of deutetrabenazine twice daily tablets.

In one embodiment, the human subject is being treated with a dose of a deutetrabenazine once daily at a total daily dose of 18 mg, and is transitioned to a total daily dose of 18 mg of deutetrabenazine twice daily tablets.

In one embodiment, the human subject is being treated with a dose of a deutetrabenazine once daily at a total daily dose of 24 mg, and is transitioned to a total daily dose of 24 mg of deutetrabenazine twice daily tablets.

In one embodiment, the human subject is being treated with a dose of a deutetrabenazine once daily at a total daily dose of 30 mg, and is transitioned to a total daily dose of 30 mg of deutetrabenazine twice daily tablets.

In one embodiment, the human subject is being treated with a dose of a deutetrabenazine once daily at a total daily dose of 36 mg, and is transitioned to a total daily dose of 36 mg of deutetrabenazine twice daily tablets.

In one embodiment, the human subject is being treated with a dose of a deutetrabenazine once daily at a total daily dose of 42 mg, and is transitioned to a total daily dose of 42 mg of deutetrabenazine twice daily tablets.

In one embodiment, the human subject is being treated with a dose of a deutetrabenazine once daily at a total daily dose of 48 mg, and is transitioned to a total daily dose of 48 mg of deutetrabenazine twice daily tablets.

In one specific embodiment, the deutetrabenazine once daily is an extended-release dosage form, preferably, an osmotic dosage form according to any one of the embodiments of the invention. In one embodiment, the deutetrabenazine once daily extended-release dosage form is administered with food or without food.

In one embodiment, a human subject is treated with a deutetrabenazine once daily osmotic dosage form and is transitioned to a deutetrabenazine twice daily dosage form.

In one embodiment, the abnormal involuntary movement being controlled during the transition from the once daily deutetrabenazine dosage form to the twice daily deutetrabenazine tablet is chorea, akathisia, dyskinesia, tremor, tic, chorea associated with Huntington's disease, tardive dyskinesia, a tic associated with Tourette syndrome, Parkinson's disease levodopa-induced dyskinesia or dyskinesia in cerebral palsy. In one embodiment, the abnormal involuntary movement being controlled is chorea associated with Huntington's disease. In one embodiment, the abnormal involuntary movement being controlled is tardive dyskinesia.

Further provided is a method of transitioning a human subject being treating with a daily amount of tetrabenazine to a once daily amount of deutetrabenazine, for control of abnormal involuntary movement from, comprising:

a) administering the last dose of tetrabenazine; and b) the next day, administering to the human subject a once daily deutetrabenazine osmotic dosage form wherein:

the daily amount of tetrabenazine is 12.5 mg and the once daily amount of deutetrabenazine is 6 mg; or wherein the daily amount of tetrabenazine is 25 mg and the once daily amount of deutetrabenazine is 12 mg; or wherein the daily amount of tetrabenazine is 37.5 mg and the once daily amount of deutetrabenazine is 18 mg; or wherein the daily amount of tetrabenazine is 50 mg and the once daily amount of deutetrabenazine is 24 mg; or wherein the daily amount of tetrabenazine is 62.5 mg and the once daily amount of deutetrabenazine is 30 mg; or wherein the daily amount of tetrabenazine is 75 mg and the once daily amount of deutetrabenazine is 36 mg; or wherein the daily amount of tetrabenazine is 87.5 mg and the once daily amount of deutetrabenazine is 42 mg; or wherein the daily amount of tetrabenazine is 100 mg and the once daily amount of deutetrabenazine is 48 mg.

In some embodiments, the daily amount of tetrabenazine is administered in divided doses, for example, in two, three, or more divided doses.

In one embodiment, the abnormal involuntary movement being controlled during the transition from tetrabenazine to once-daily dose of deutetrabenazine is chorea, akathisia, dyskinesia, tremor, tic, chorea associated with Huntington's disease, tardive dyskinesia, a tic associated with Tourette syndrome, Parkinson's disease levodopa-induced dyskinesia or dyskinesia in cerebral palsy. In one embodiment, the abnormal involuntary movement being controlled is chorea associated with Huntington's disease. In one embodiment, the abnormal involuntary movement being controlled is tardive dyskinesia.

In one embodiment, the once daily deutetrabenazine extended-release dosage form is administered with food or without food.

The present disclosure provides oral dosage forms and methods, according to any of the following aspects:

Aspects

1. An osmotic dosage form for once daily administration to a subject in need thereof comprising:
   a. a tablet core comprising an active layer comprising an amount of deutetrabenazine microparticles and a push layer;
   b. a semipermeable layer surrounding the tablet core; and
   c. a port extending from the periphery of the dosage form into the tablet core.
2. The dosage form of Aspect 1, wherein the active layer further comprises an active layer control release agent.
3. The dosage form of Aspect 2, wherein the active layer control release agent comprises a polymer having a viscosity of about 50-150 mPa s or about 55-90 mPa s.
4. The dosage form of Aspect 2 or Aspect 3, wherein the active layer control release agent comprises at least one of a polyoxyethylene polymer, an ionic hydrogel, a hydrophilic polymer, a hydrophobic polymer or any mixture thereof
5. The dosage form of Aspect 4, wherein the active layer control release agent comprises a polyoxyethylene polymer that is polyethylene oxide.
6. The dosage form of Aspect 5, wherein the polyethylene oxide within the active layer has an average molecular weight of 100,000 daltons to 500,000 daltons.
7. The dosage form of Aspect 6, wherein the polyethylene oxide within the active layer has an average molecular weight of 200,000 daltons.
8. The dosage form of any one of Aspects 2-7, wherein the active layer control release agent is present in the active layer in an amount of about 60% to about 98% by weight, based on the total weight of the active layer.
9. The dosage form of Aspect 8, wherein the active layer control release agent is present in the active layer in an amount of about 70% to about 95% by weight, based on the total weight of the active layer, or about 80% to about 90%, or about 85% to about 95%, by weight, based on the total weight of the active layer.
10. The dosage form of any one of Aspects 2-9, wherein the weight ratio of the amount of deutetrabenazine microparticles and the active layer control release agent in the active layer is 2:3-1:50 or 2:5-1:5 or 1:4-1:9 or 1:5-1:19 or 1:5-1:7 or 1:12-1:15 or 1:20-1:30.
11. The dosage form of any preceding Aspect, wherein the active layer further comprises at least one active layer antioxidant.
12. The dosage form of Aspect 11, wherein the active layer antioxidant comprises at least one of tertiary butyl-4-methoxyphenol (mixture of 2 and 3-isomers), 2,6-ditertiary butyl-p-cresol, propyl gallate, 6-ethoxy-1,2-digydro-2,2,4-trimethylquinoline (ethoxyquin), nordihydroguaiaretic acid (NDGA), butylated hydroxyanisole, butylated hydroxytoluene or any mixture thereof
13. The dosage form of Aspect 12, wherein the active layer antioxidant comprises a mixture of butylated hydroxyanisole and butylated hydroxytoluene.
14. The dosage form of any one of Aspects 11-13, wherein the active layer antioxidant is present in the active layer in an amount of about 0.001% to about 1% by weight, based on the total weight of the active layer.
15. The dosage form of any preceding Aspect, wherein the active layer further comprises at least one of active layer binder.

16. The dosage form of Aspect 15, wherein the active layer binder comprises at least one of hypromellose (hydroxypropyl methylcellulose), starch, gelatin, agar, natural or synthetic gums or any mixture thereof
17. The dosage form of Aspect 16, wherein the active layer binder comprises hypromellose.
18. The dosage form of any one of Aspects 15-17, wherein the active layer binder is present in the active layer in an amount of about 2% to about 20% by weight, based on the total weight of the active layer.
19. The dosage form of any preceding Aspect, wherein the active layer further comprises one or more pharmaceutically acceptable excipients.
20. The dosage form of any preceding Aspect, wherein the active layer comprises deutetrabenazine microparticles, and an active layer control release agent which is a polymer having a viscosity of about 55-90 mPa s and an antioxidant.
21. The dosage form of Aspect 20, wherein the active layer comprises deutetrabenazine microparticles, butylated hydroxyanisole, butylated hydroxytoluene, polyethylene oxide, hypromellose and magnesium stearate.
22. The dosage form of any preceding Aspect, wherein the push layer comprises an osmotic agent and a push layer control release agent.
23. The dosage form of Aspect 22, wherein the osmotic agent comprises an inorganic salt, a carbohydrate or any mixture thereof
24. The dosage form of Aspect 23, wherein the osmotic agent comprises a carbohydrate that is d-mannitol, sorbitol, inositol, a monosaccharide, an oligosaccharide, a polysaccharide, or any mixture thereof
25. The dosage form of Aspect 23, wherein the osmotic agent comprises an inorganic salt that is magnesium sulfate, magnesium chloride, potassium sulfate, sodium chloride, sodium sulfate, lithium sulfate, sodium phosphate, potassium phosphate, or any mixture thereof
26. The dosage form of Aspect 25, wherein the osmotic agent is/comprises? sodium chloride.
27. The dosage form of any one of Aspects 22-26, wherein the osmotic agent is present in the dosage form in an amount of about 5% to about 50% by weight, based on the total weight of the dosage form.
28. The dosage form of Aspect 27, wherein the osmotic agent is present in the dosage form in an amount of about 5% to about 20% by weight, based on the total weight of the dosage form.
29. The dosage form of Aspect 27 or Aspect 28, wherein the osmotic agent is present in the dosage form in an amount of about 8% to about 10% by weight, based on the total weight of the dosage form.
30. The dosage form of any one of Aspects 27-29, wherein the osmotic agent is present in the push layer in an amount of about 20% to about 40% by weight, based on the total weight of the push layer.
31. The dosage form of Aspect 30, wherein the osmotic agent is present in the push layer in an amount of about 30% by weight, based on the total weight of the push layer.
32. The dosage form of any one of Aspects 22-31, wherein the push layer control release agent comprises a polymer having a viscosity of about 5500-7500 mPa s.
33. The dosage form of Aspect 32, wherein the polymer having a viscosity of about 5500-7500 mPa s is selected from a polyoxyethylene polymer, an ionic hydrogel, a hydrophilic polymer, a hydrophobic polymer or any mixture thereof

34. The dosage form of Aspect 33, wherein the push layer control release agent is a polyethylene oxide.

35. The dosage form of Aspect 34, wherein the polyethylene oxide within the push layer has an average molecular weight of 1,000,000 daltons to 7,000,000 daltons.

36. The dosage form of Aspect 35 wherein the polyethylene oxide within the push layer has an average molecular weight of 5,000,000 daltons.

37. The dosage form of any one of Aspect 32-36, wherein the push layer control release agent is present in the push layer in an amount of about 50% to about 80% by weight, based on the total weight of the push layer.

38. The dosage form of Aspect 37, wherein the push layer control release agent is present in the push layer in an amount of about 60% to about 70% by weight, based on the total weight of the push layer.

39. The dosage form of any one of Aspects 22-38, wherein the weight ratio of the osmotic agent and the push layer control release agent in the push layer is 1:2-1:3.5 or 1:2-1:2.5.

40. The dosage form of any one of Aspects 22-39, wherein the push layer further comprises a push layer binder.

41. The dosage form of Aspect 40, wherein the push layer binder comprises hypromellose (hydroxypropyl methylcellulose), starch, gelatin, agar, natural or synthetic gums, or any mixture thereof 42. The dosage form of Aspect 41, wherein the push layer binder comprises hypromellose.

43. The dosage form of any one of Aspects 40-42, wherein the push layer binder is present in the push layer in an amount of about 2% to about 10% by weight, based on the total weight of the push layer.

44. The dosage form of Aspect 43, wherein the push layer binder is present in the push layer in an amount of about 4% to about 6% by weight, based on the total weight of the push layer or about 3% to about 6% by weight, based on the total weight of the push layer.

45. The dosage form of any one of Aspects 22-44, wherein the push layer further comprises a pharmaceutically acceptable excipient.

46. The dosage form of any one of Aspects 22-45, wherein the push layer comprises sodium chloride and a polymer having a viscosity of about 5500-7500 mPa s.

47. The dosage form of Aspect 46, wherein the push layer comprises sodium chloride, polyethylene oxide, hydroxypropyl methylcellulose, a colorant, and magnesium stearate.

48. The dosage form of any preceding Aspect, wherein the semipermeable layer comprises a water soluble polymer, a water insoluble polymer or any mixture thereof 49. The dosage form of Aspect 48, wherein the semipermeable layer comprises a water insoluble polymer selected from cellulose acetate, cellulose diacetate, cellulose triacetate, cellulose propionate, cellulose acetate butyrate, cellulose ethers like ethyl cellulose, agar acetate, amylose triacetate, betaglucan acetate, poly(vinyl methyl) ether copolymers, poly(orthoesters), poly acetals and selectively permeable poly (glycolic acid), poly(lactic acid) derivatives, Eudragit cellulose acetate or any mixture thereof 50. The dosage form of Aspect 49, wherein the water insoluble polymer is cellulose acetate, comprising 32%-39.8% acetyl content.

51. The dosage form of any preceding Aspect, wherein the semipermeable layer comprises cellulose acetate and polyethylene glycol.

52. The dosage form of any one of Aspects 48-51, wherein the water insoluble polymer is present in the semipermeable layer in an amount of about 80% to about 99.9% by weight, based on the weight of the semipermeable layer or about 85% to about 95% by weight, based on the weight of the semipermeable layer.

53. The dosage form of any preceding Aspect, wherein the semipermeable layer comprises a pore-forming agent.

54. The dosage form of Aspect 53, wherein the pore-forming comprises a water soluble sugar, a water soluble salt, a water soluble solvent, a water soluble polymer or any mixture thereof 55. The dosage form of Aspect 54, wherein the pore-forming agent is a water soluble solvent which is polyethylene glycol.

56. The dosage form of any one of Aspects 53-55, wherein the pore-forming agent is present in the semipermeable layer in an amount of about 0.1% to about 20% by weight of the semipermeable layer.

57. The dosage form of Aspect m 56, wherein the pore-forming agent is present in the semipermeable layer in an amount of about 8% to about 15% by weight of the semipermeable layer.

58. The dosage form of any preceding Aspect, wherein the weight ratio of the semipermeable layer and the tablet core is 1:8-1:10.

59. The dosage form of any preceding Aspect, wherein the port has a diameter of from about 0.1 mm to about 1 mm.

60. The dosage form of Aspect 59, wherein the port has a diameter of from about 0.4 mm to about 0.8 mm.

61. The dosage form of any preceding Aspect, further comprising a tablet core seal coat on the outer surface of the tablet core.

62. The dosage form of any preceding Aspect, further comprising a semipermeable layer seal coat on the outer surface of the semipermeable layer.

63. The dosage form of any one of Aspect 61-62, wherein the tablet core seal coat and or the semipermeable layer seal coat comprises a binder.

64. The dosage form of Aspect 63, wherein the tablet core seal coat binder and or the semipermeable layer seal coat binder comprise: hypromellose (hydroxypropyl methylcellulose), starch, gelatin, agar, natural gums, synthetic gums and any mixture thereof 65. The dosage form of Aspect 64, wherein the tablet core seal coat binder and or the semipermeable layer seal coat binder is hypromellose.

66. The dosage form of any one of Aspects 63-65, wherein the total amount of the binder within the dosage form is about 0 to about 20% by weight, based on the total weight of the dosage form; 5% to about 15% by weight, based on the total weight of the dosage form; or 5% to about 20% by weight, based on the total weight of the dosage form.

67. The dosage form of Aspect 66, wherein the total amount of the binder within the dosage form is about 8% to about 10% by weight, based on the total weight of the dosage form or about 10% to about 20% by weight, based on the total weight of the dosage form, or about 10% to about 20% by weight, based on the total weight of the dosage form.

68. The dosage form of any preceding Aspect, further comprising an immediate release coating external to the semipermeable membrane, the immediate release coating comprising a second amount of deutetrabenazine microparticles.

69. The dosage form of Aspect 68, wherein the immediate release coating comprises about 0.1% to about 25% by weight deutetrabenazine microparticles, based on the total weight of the dosage form or about 0.2% to about 5% by weight deutetrabenazine microparticles, based on the total weight of the dosage form or about 0.3% to about 2% by weight deutetrabenazine microparticles, based on the total weight of the dosage form.

70. The dosage form of Aspect 69, wherein the dosage form comprises a total of 24 mg of deutetrabenazine microparticles and the immediate release coating comprises about 1% to about 2% by weight deutetrabenazine microparticles, based on the total weight of the dosage form or wherein the dosage form comprises a total of 12 mg of deutetrabenazine microparticles and the immediate release coating comprises about 0.5% to about 1% by weight deutetrabenazine microparticles, based on the total weight of the dosage form or wherein the dosage form comprises a total of 6 mg of deutetrabenazine microparticles and the immediate release coating comprises about 0.1% to about 0.5% by weight deutetrabenazine microparticles, based on the total weight of the dosage form.

71. The dosage form of any preceding Aspect, wherein about 70% to 99% of the total amount of deutetrabenazine microparticles in the dosage form, is within the active layer.

72. The dosage form of any preceding Aspect, wherein about 5% to 30% of the total amount of deutetrabenazine microparticles in the dosage form, is within immediate release coating.

73. The dosage form of any preceding Aspect, wherein about 70%-80% of the total amount of deutetrabenazine microparticles in the dosage form, is within the active layer and wherein about 20%-30% of the total amount of deutetrabenazine microparticles in the dosage form, is within immediate release coating.

74. The dosage form of any one of Aspects 68-73, wherein the immediate release coating further comprises an immediate release coating antioxidant.

75. The dosage form of Aspect 74, wherein the immediate release coating antioxidant comprises: tertiary butyl-4-methoxyphenol (mixture of 2 and 3-isomers), 2,6-ditertiary butyl-p-cresol, propyl gallate, 6-ethoxy-1,2-digydro-2,2,4-trimethylquinoline (ethoxyquin), nordihydroguaiaretic acid (NDGA), butylated hydroxyanisole, butylated hydroxytoluene and any mixture thereof 76. The dosage form of Aspect 75, wherein the immediate release coating comprises a mixture of butylated hydroxyanisole, and butylated hydroxytoluene.

77. The dosage form of any one of Aspects 68-76, wherein the immediate release coating further comprises an additional pharmaceutically acceptable excipient.

78. The dosage form of any one of Aspects 68-77, wherein the immediate release coating comprises: deutetrabenazine microparticles, butylated hydroxyanisole, butylated hydroxytoluene, hypromellose and polysorbate 80.

79. The dosage form of any preceding Aspect, wherein the total amount of deutetrabenazine microparticles in the dosage form is from about 6 mg to about 48 mg.

80. The dosage form of any preceding Aspect, wherein the total amount of deutetrabenazine microparticles in the dosage form is about 6 mg.

81. The dosage form of any preceding Aspect, wherein the total amount of deutetrabenazine microparticles in the dosage form is about 12 mg.

82. The dosage form of any preceding Aspect, wherein the total amount of deutetrabenazine microparticles in the dosage form is about 24 mg.

83. The dosage form of any preceding Aspect, wherein the total amount of deutetrabenazine microparticles in the dosage form is about 48 mg.

84. The dosage form of any preceding Aspect, wherein the total amount of deutetrabenazine microparticles is about 0.5% to about 15% by weight, based on the total weight of the dosage form.

85. The dosage form of Aspect 84, wherein the total amount of deutetrabenazine microparticles is about 1% to about 10% by weight, based on the total weight of the dosage form.

86. The dosage form of Aspect 85, comprising a total of 6 mg of deutetrabenazine microparticles, wherein the total amount of deutetrabenazine microparticles is about 0.5% to about 3% by weight, based on the total weight of the dosage form or a dosage form comprising a total of 12 mg of deutetrabenazine microparticles, wherein the total amount of deutetrabenazine microparticles is about 1% to about 5% by weight, based on the total weight of the dosage form or a dosage form comprising a total of 24 mg of deutetrabenazine microparticles, wherein the total amount of deutetrabenazine microparticles is about 5% to about 10% by weight, based on the total weight of the dosage form.

87. The dosage form of any preceding Aspect, wherein the deutetrabenazine microparticles have a particle size of about 1 μm to about 30 μm in diameter.

88. The dosage form of Aspect 87, wherein the deutetrabenazine microparticles have a particle size providing a $D_{90}$ of 15 μm.

89. The dosage form of Aspect 87 or Aspect 88, wherein the deutetrabenazine microparticles have a particle size providing a $D_{50}$ 10 μm.

90. The dosage form of any one of Aspects 87-89, wherein the deutetrabenazine microparticles have a particle size providing a $D_{10}$ of 3 μm.

91. A method of treating a hyperkinetic movement disorder in a subject in need thereof comprising orally administering, on a once daily basis to the subject, an osmotic dosage form according to any one of the preceding Aspects.

92. The method of Aspect 91, wherein the movement disorder is selected from chorea, akathisia, dyskinesia, tremor, and tic.

93. The method of Aspect 92, wherein the movement disorder is selected from chorea associated with Huntington's disease, tardive dyskinesia, a tic associated with Tourette syndrome, Parkinson's disease levodopa-induced dyskinesia and dyskinesia in cerebral palsy.

94. The method of any one of Aspects 91-93, comprising orally administering to the subject a once daily osmotic dosage form according to any one of Aspects 1-90, wherein single dose administration of the osmotic dosage form, which comprises a total amount of 6 mg of deutetrabenazine microparticles provides an in vivo plasma profile for total α- and β-dihydrodeutetrabenazine that includes a geometric mean $AUC_{0-inf}$ of about 91,250 to 142,750 h*pg/mL.

95. The method of any one of Aspects 91-94, comprising orally administering to the subject a once daily osmotic dosage form according to any one of Aspects 1-90, wherein single dose administration of the osmotic dosage form, which comprises a total amount of 6 mg of deutetrabenazine microparticles provides an in vivo plasma profile for total α- and β-dihydrodeutetrabenazine that includes a geometric mean $C_{max}$ of less than about 4,600 pg/mL.

96. The method of any one of Aspects 91-93, comprising orally administering to the subject a once daily osmotic dosage form according to any one of Aspects 1-90, wherein single dose administration of the osmotic dosage form, which comprises a total amount of 12 mg of deutetrabenazine microparticles, provides an in vivo plasma profile for total α- and β-dihydrodeutetrabenazine that includes a geometric mean $AUC_{0-inf}$ of about 182,500 to 285,500 h*pg/mL.

97. The method of any one of Aspects 91-93 or 96, comprising orally administering to the subject a once daily osmotic dosage form according to any one of Aspects 1-90, wherein single dose administration of the osmotic dosage form, which comprises a total amount of 12 mg of deutetrabenazine microparticles, provides an in vivo plasma profile for total α- and β-dihydrodeutetrabenazine that includes a geometric mean $C_{max}$ of less than about 9,200 pg/mL.

98. The method of any one of Aspects 91-93, comprising orally administering to the subject a once daily osmotic dosage form according to any one of Aspects 1-90, wherein single dose administration of the osmotic dosage form, which comprises a total amount of 24 mg of deutetrabenazine microparticles, provides an in vivo plasma profile for total α- and β-dihydrodeutetrabenazine that includes a geometric mean $AUC_{0-inf}$ of about 365,000 to 571,000 h*pg/mL.

99. The method of any one of Aspects 91-93 or Aspect 98 comprising orally administering to the subject a once daily osmotic dosage form according to any one of Aspects 1-90, wherein single dose administration of the osmotic dosage form, which comprises a total amount of 24 mg of deutetrabenazine microparticles, provides an in vivo plasma profile for total α- and β-dihydrodeutetrabenazine that includes a geometric mean $C_{max}$ of less than about 18,400 pg/mL.

100. The method of any one of Aspects 91-93, comprising orally administering to the subject a once daily osmotic dosage form according to any one of Aspects 1-90, wherein single dose administration of the osmotic dosage form, which comprises a total amount of 36 mg of deutetrabenazine microparticles, provides an in vivo plasma profile for total α- and β-dihydrodeutetrabenazine that includes a geometric mean $AUC_{0-inf}$ of about 547,500 to 856,500 h*pg/mL.

101. The method of any one of Aspects 91-93 or Aspect 100, comprising orally administering to the subject a once daily osmotic dosage form according to any one of Aspects 1-90, wherein single dose administration of the osmotic dosage form, which comprises a total amount of 36 mg of deutetrabenazine microparticles, provides an in vivo plasma profile for total α- and β-dihydrodeutetrabenazine that includes a geometric mean $C_{max}$ of less than about 27,600 pg/mL.

102. The method of any one of Aspects 91-93, comprising orally administering to the subject a once daily osmotic dosage form according to any one of Aspects 1-90, wherein single dose administration of the osmotic dosage form, which comprises a total amount of 48 mg of deutetrabenazine microparticles, provides an in vivo plasma profile for total α- and β-dihydrodeutetrabenazine that includes a geometric mean $AUC_{0-inf}$ of about 730,000 to 1,142,000 h*pg/mL.

103. The method of any one of Aspects 91-93 or Aspect 102, comprising orally administering to the subject a once daily osmotic dosage form according to any one of Aspects 1-90, wherein single dose administration of the osmotic dosage form, which comprises a total amount of 48 mg of deutetrabenazine microparticles, provides an in vivo plasma profile for total α- and β-dihydrodeutetrabenazine that includes a geometric mean $C_{max}$ of less than about 36,800 pg/mL.

104. The method of any one of Aspects 91-93, comprising orally administering to the subject a once daily osmotic dosage form according to any one of Aspects 1-90 wherein the osmotic dosage form which comprises a total amount of 6 mg of deutetrabenazine microparticles, provides an in vivo plasma profile for total α- and β-dihydrodeutetrabenazine at steady state that includes a mean $AUC_{0-24}$ of about 102,500 to 200,000 h*pg/mL.

105. The method of any one of Aspects 91-93 or Aspect 104, comprising orally administering to the subject a once daily osmotic dosage form according to any one of Aspects 1-90 wherein the osmotic dosage form which comprises a total amount of 6 mg of deutetrabenazine microparticles, provides an in vivo plasma profile for total α- and β-dihydrodeutetrabenazine at steady state that includes a mean $C_{max}$ of less than about 10,000 pg/mL.

106. The method of any one of Aspects 91-93, comprising orally administering to the subject a once daily osmotic dosage form according to any one of Aspects 1-90 wherein the osmotic dosage form which comprises a total amount of 12 mg of deutetrabenazine microparticles provides an in vivo plasma profile for total α- and β-dihydrodeutetrabenazine at steady state that includes a mean $AUC_{0-24}$ of about 205,000 to 400,000 h*pg/mL.

107. The method of any one of Aspects 91-93 or Aspect 106, comprising orally administering to the subject a once daily osmotic dosage form according to any one of Aspects 1-90 wherein the osmotic dosage form which comprises a total amount of 12 mg of deutetrabenazine microparticles provides an in vivo plasma profile for total α- and β-dihydrodeutetrabenazine at steady state that includes a mean $C_{max}$ of less than about 20,000 pg/mL.

108. The method of any one of Aspects 91-93, comprising orally administering to the subject a once daily osmotic dosage form according to any one of Aspects 1-90 wherein the osmotic dosage form which comprises a total amount of 24 mg of deutetrabenazine microparticles, provides an in vivo plasma profile for total α- and β-dihydrodeutetrabenazine at steady state that includes a mean $AUC_{0-24}$ of about 410,000 to 800,000 h*pg/mL.

109. The method of any one of Aspects 91-93 or Aspect 108 comprising orally administering to the subject a once daily osmotic dosage form according to any one of Aspects 1-90 wherein the osmotic dosage form which comprises a total amount of 24 mg of deutetrabenazine microparticles, provides an in vivo plasma profile for total α- and β-dihydrodeutetrabenazine at steady state that includes a mean $C_{max}$ of less than about 40,000 pg/mL.

110. The method of any one of Aspects 91-93, comprising orally administering to the subject a once daily osmotic dosage form according to any one of Aspects 1-90 wherein the osmotic dosage form which comprises a total amount of 36 mg of deutetrabenazine microparticles, provides an in vivo plasma profile for total $\alpha$- and $\beta$-dihydrodeutetrabenazine at steady state that includes a mean $AUC_{0\text{-}24}$ of about 615,000 to 1,200,000 h*pg/mL.

111. The method of any one of Aspects 91-93 or Aspect 110, comprising orally administering to the subject a once daily osmotic dosage form according to any one of Aspects 1-90 wherein the osmotic dosage form which comprises a total amount of 36 mg of deutetrabenazine microparticles, provides an in vivo plasma profile for total $\alpha$- and $\beta$-dihydrodeutetrabenazine at steady state that includes a mean $C_{max}$ of less than about 60,000 pg/mL.

112. The method of any one of Aspects 91-93, comprising orally administering to the subject a once daily osmotic dosage form according to any one of Aspects 1-90 wherein the osmotic dosage form which comprises a total amount of 48 mg of deutetrabenazine microparticles, provides an in vivo plasma profile for total $\alpha$- and $\beta$-dihydrodeutetrabenazine at steady state that includes a mean $AUC_{0\text{-}24}$ of about 820,000 to 1,600,000 h*pg/mL.

113. The method of any one of Aspects 91-93 or Aspect 112, comprising orally administering to the subject a once daily osmotic dosage form according to any one of Aspects 1-90 wherein the osmotic dosage form which comprises a total amount of 48 mg of deutetrabenazine microparticles, provides an in vivo plasma profile for total $\alpha$- and $\beta$-dihydrodeutetrabenazine at steady state that includes a mean $C_{max}$ of less than about 80,000 pg/mL.

114. The method of any one of Aspects 91-113, comprising administering an osmotic dosage form according to any one of Aspects 1-90, wherein not more than 15% of the drug formulation is released after 2 hours when tested in 500 mL acid phosphate buffer at pH 3.0 using a USP II dissolution apparatus.

115. The method of any one of Aspects 91-113, comprising administering an osmotic dosage form according to any one of Aspects 1-90, wherein not more than 60% of the drug formulation is released after 8 hours when tested in 500 mL acid phosphate buffer at pH 3.0 using a USP II dissolution apparatus.

116. The dosage form or method of any preceding Aspect, wherein the dosage form is administered with food.

117. The dosage form or method of any one of Aspects 1-115, wherein the dosage form is administered under fasting conditions.

All patents, patent applications, and publications are herein incorporated by reference to the same extent as if each individual publication was specifically and individually indicated to be incorporated by reference. The invention illustratively described herein may be practiced in the absence of any element(s) not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

For the foregoing embodiments, each embodiment disclosed herein is contemplated as being applicable to each of the other disclosed embodiments. For instance, the elements recited in the method embodiments can be used in the pharmaceutical composition, package, and use/method embodiments described herein and vice versa.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the disclosure.

Example 1—Manufacturing Process for Osmotic Tablets, 24 mg Deutetrabenazine

Figure 2A:
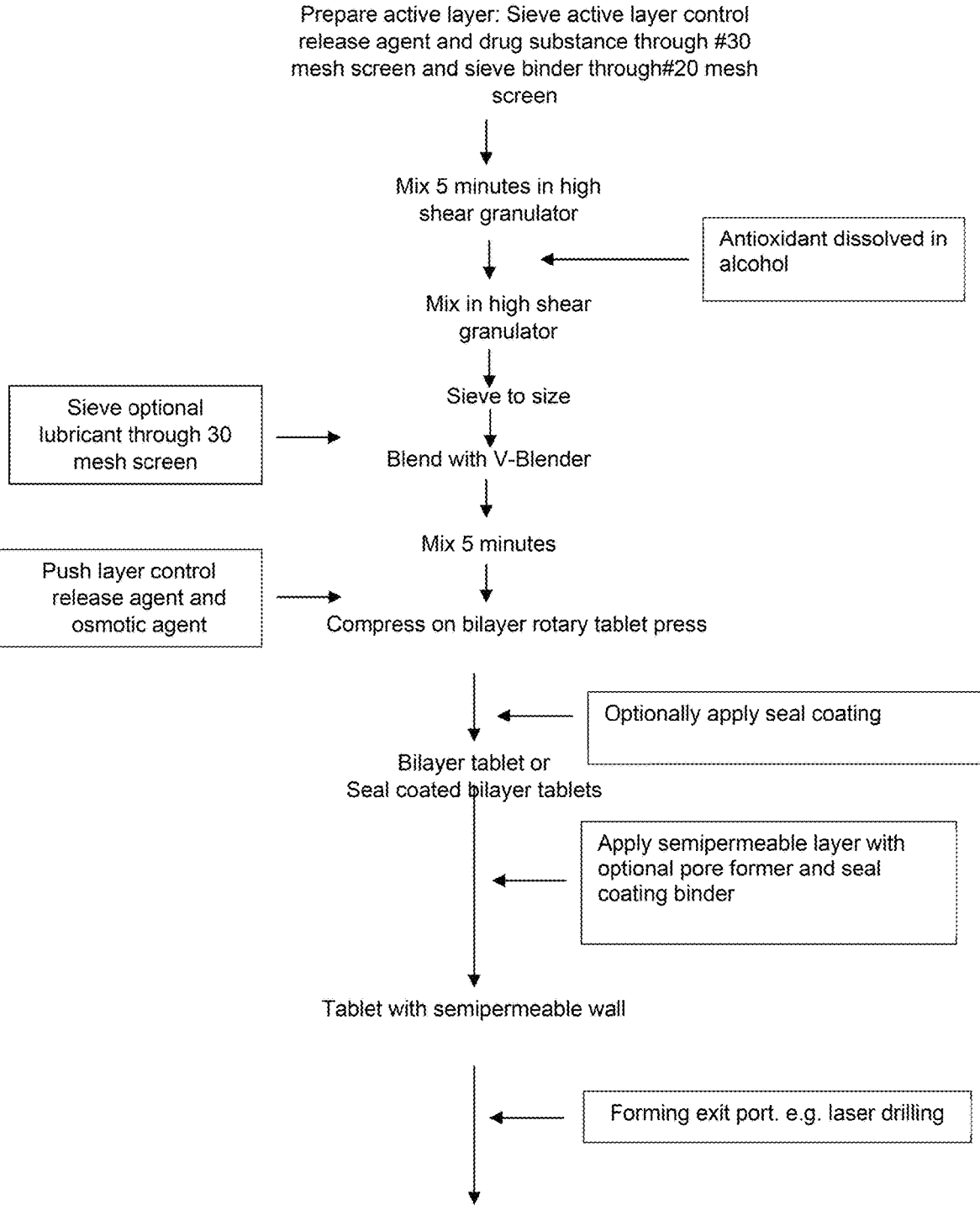
FIG. 2a and FIG. 2b provide flowcharts of the general manufacturing processes for osmotic dosage forms according to the present disclosure.
Figure 2B:
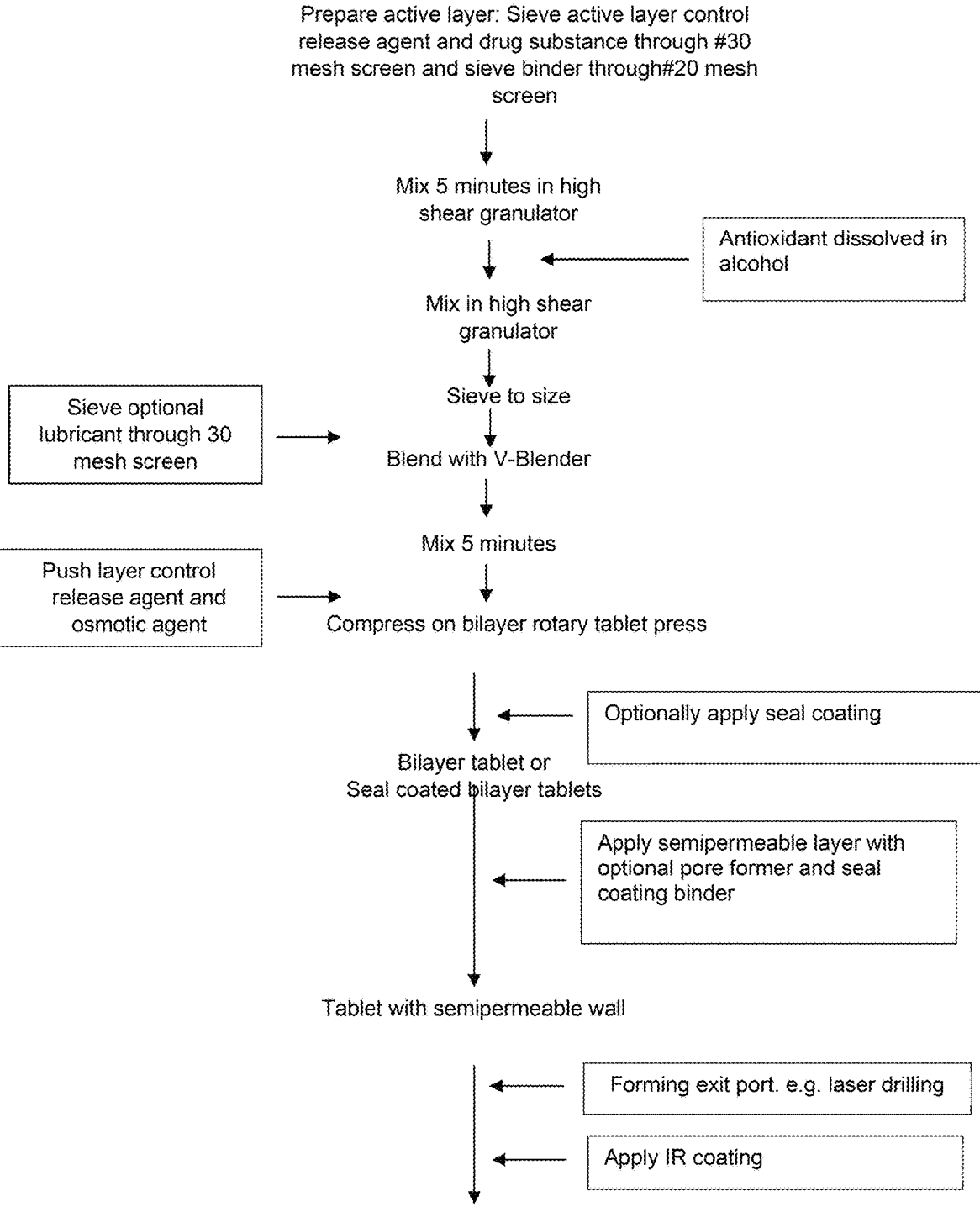

FIG. 2*a* and FIG. 2*b* provide flowcharts of the general manufacturing processes for osmotic dosage forms according to the present disclosure. Tables 1-13, below, provide non-limiting examples of the materials and their relative amounts used to produce the dosage forms described herein. The preparation method was as follows:

A: Active layer materials processing: deutetrabenazine (micronized) and the active layer control release agent were passed through a #30 mesh screen and combined with a binder (previously passed through a #20 mesh screen). The mixture was introduced into a high shear granulator and dry mixed for about 5 minutes. While mixing, antioxidant (pre dissolved in alcohol) was added to the mixing powders to granulate the material. Additional mixing continued until the desired granulation end-point was achieved. The resulting granulation is wet screened to break up any oversized agglomerates. The material was fed into a diffusive mixer (V-Blender) where it was blended for about 15 minutes. Lubricant that had been passed through a #30 mesh screen was added to the blended material in the V-Blender. The contents were lubricated for about 5 minutes.

B: Tablet core compression: the active layer materials were discharged into a bilayer rotary tablet press. The push layer materials (osmotic agent, push layer control release agent and optionally a binder, a colorant and a lubricant) were combined and further fed into the bilayer rotary tablet press. The tablet core was compressed.

C: Optional tablet core seal coat: A tablet core seal coat comprising a binder solution was applied on the tablet core.

D: Semipermeable layer: Semipermeable layer comprising a solution of cellulose acetate and an optional pore-forming agent was applied to the tablet core, or sealed tablet core, using a pan coater.

E: Optional Semipermeable layer seal coat: Semipermeable layer seal coat comprising a binder solution was applied on the tablet compromising the semipermeable wall.

F: Creating an exit means: a pore was laser-drilled through the layers into the active layer.

A final immediate release coating comprising deutetrabenazine is optionally applied, using similar materials and following the processing steps as detailed above for active layer.

TABLE 1

| Component | Amount (mg) |
| --- | --- |
| Deutetrabenazine (micronized) | 24.00 |
| Polyethylene Oxide, NF (Polyox ® WSR N80) | 123 |
| Polyethylene Oxide, NF (FP) (Polyox ® WSR Coagulant, Fine Powder) | 56.23 |
| Hypromellose 2910 | 8.6 |
| Magnesium Stearate | 0.87 |
| Sodium Chloride, USP (Powder) | 21.91 |
| Hydroxypropyl Cellulose NF (Klucel ® EXF) | 3.16 |
| FD&C Red No. 40 Aluminum Lake HT 38%-42% | 0.23 |
| Cellulose Acetate, NF 398-10 | 11.87 |
| Cellulose Acetate, NF 320S | 0.62 |
| Polyethylene Glycol 3350 | 0.62 |
| Purified Water, USP | n.a. |
| Acetone | n.a. |
| Total | 251.11 |

TABLE 2

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Polyethylene Oxide, NF (Polyox ® WSR N80) | 123 |
| Polyethylene Oxide, NF (FP) (Polyox ® WSR Coagulant, Fine Powder) | 56.23 |
| Methocel ® E5 Premium (Hypromellose 2910, USP) | 8.6 |
| Magnesium Stearate | 0.87 |
| Sodium Chloride, USP (Powder) | 21.91 |
| Hydroxypropyl Cellulose NF (Klucel ® EXF) | 3.16 |
| FD&C Red No. 40 Aluminum Lake HT 38%-42% | 0.23 |
| Cellulose Acetate, NF 398-10 | 18.09 |
| Cellulose Acetate, NF 320S | 0.95 |
| Polyethylene Glycol 3350 | 1.9 |
| Purified Water, USP | n.a. |
| Acetone | n.a. |
| Total | 260.34 |

TABLE 3

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Polyethylene Oxide, NF (Polyox ® WSR N80) | 123 |
| Polyethylene Oxide, NF (FP) (Polyox ® WSR Coagulant, Fine Powder) | 71.73 |
| Methocel ® E5 Premium (Hypromellose 2910, USP) | 16.1 |
| Magnesium Stearate | 1 |
| Sodium Chloride, USP (Powder) | 27.94 |
| Hydroxypropyl Cellulose NF (Klucel ® EXF) | 4.03 |
| FD&C Red No. 40 Aluminum Lake HT 38%-42% | 0.3 |
| Cellulose Acetate, NF 398-10 | 21.38 |
| Cellulose Acetate, NF 320S | 2.37 |
| Polyethylene Glycol 3350 | 2.77 |
| Purified Water, USP | n.a. |
| Acetone | n.a. |
| Total | 296 |

TABLE 4

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Polyethylene Oxide, NF (Polyox ® WSR N80) | 123 |
| Polyethylene Oxide, NF (FP) (Polyox ® WSR Coagulant, Fine Powder) | 80.23 |
| Methocel ® E5 Premium (Hypromellose 2910, USP) | 16.92 |
| Magnesium Stearate | 1.07 |
| Sodium Chloride, USP (Powder) | 48.86 |
| Hydroxypropyl Cellulose NF (Klucel ® EXF) | 4.51 |
| FD&C Red No. 40 Aluminum Lake HT 38%-42% | 0.33 |
| Cellulose Acetate, NF 398-10 | 23.82 |
| Cellulose Acetate, NF 320S | 2.64 |
| Polyethylene Glycol 3350 | 3.08 |
| Purified Water, USP | n.a. |
| Acetone | n.a. |
| Total | 329.87 |

TABLE 5

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Polyethylene Oxide, NF (Polyox ® WSR N80) | 123 |
| Polyethylene Oxide, NF (FP) (Polyox ® WSR Coagulant, Fine Powder) | 82.29 |
| Methocel ® E5 Premium (Hypromellose 2910, USP) | 22.15 |
| Magnesium Stearate | 1.09 |
| Sodium Chloride, USP (Powder) | 49.66 |
| Hydroxypropyl Cellulose NF (Klucel ® EXF) | 4.63 |
| FD&C Red No. 40 Aluminum Lake HT 38%-42% | 0.34 |
| Cellulose Acetate, NF 398-10 | 24.47 |
| Cellulose Acetate, NF 320S | 2.72 |
| Polyethylene Glycol 3350 | 3.17 |
| Purified Water, USP | n.a. |
| Acetone | n.a. |
| Total | 338.92 |

TABLE 6

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Simethicone 30% Emulsion, USP | 2 |
| Lactose Monohydrate | 41 |
| Sodium Lauryl Sulfate, NF | 12.7 |
| Sodium Bicarbonate | 1 |
| Polyethylene Oxide, NF (Polyox ® WSR N80) | 123 |
| Polyethylene Oxide, NF (FP) (Polyox ® WSR Coagulant, Fine Powder) | 101.5 |
| Methocel ® E5 Premium (Hypromellose 2910, USP) | 19.67 |
| Magnesium Stearate | 1.4 |
| Sodium Chloride, USP (Powder) | 39.5 |
| Hydroxypropyl Cellulose NF (Klucel ® EXF) | 11.7 |
| FD&C Red No. 40 Aluminum Lake HT 38%-42% | 0.4 |
| Cellulose Acetate, NF 398-10 | 41 |
| Cellulose Acetate, NF 320S | 4.56 |
| Polyethylene Glycol 3350 | 4.56 |
| Purified Water, USP | n.a. |
| Acetone | n.a. |
| Total | 429.39 |

TABLE 7

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Simethicone 30% Emulsion, USP | 2 |
| Lactose Monohydrate | 41 |
| Sodium Lauryl Sulfate, NF | 12.7 |
| Edetate Disodium Dihydrate | 10 |
| Sodium Bicarbonate | 1 |
| Polyethylene Oxide, NF (Polyox ® WSR N80) | 123 |
| Polyethylene Oxide, NF (FP) (Polyox ® WSR Coagulant, Fine Powder) | 71.7 |
| Methocel ® E5 Premium (Hypromellose 2910, USP) | 18.65 |
| Magnesium Stearate | 1.2 |
| Sodium Chloride, USP (Powder) | 27.9 |
| Hydroxypropyl Cellulose NF (Klucel ® EXF) | 10 |
| FD&C Red No. 40 Aluminum Lake HT 38%-42% | 0.3 |
| Cellulose Acetate, NF 398-10 | 43.46 |
| Cellulose Acetate, NF 320S | 4.83 |
| Polyethylene Glycol 3350 | 4.83 |
| Purified Water, USP | n.a. |
| Acetone | n.a. |
| Total | 398 |

TABLE 8

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Simethicone 30% Emulsion, USP | 2 |
| Lactose Monohydrate | 41 |
| Sodium Lauryl Sulfate, NF | 12.7 |
| Edetate Disodium Dihydrate | 5 |
| Ascorbic acid | 5 |
| Sodium Bicarbonate | 1 |
| Polyethylene Oxide, NF (Polyox ® WSR N80) | 123 |
| Polyethylene Oxide, NF (FP) (Polyox ® WSR Coagulant, Fine Powder) | 71.7 |
| Methocel ® E5 Premium (Hypromellose 2910, USP) | 18.65 |
| Magnesium Stearate | 1.2 |
| Sodium Chloride, USP (Powder) | 27.9 |
| Hydroxypropyl Cellulose NF (Klucel ® EXF) | 10 |
| FD&C Red No. 40 Aluminum Lake HT 38%-42% | 0.3 |
| Cellulose Acetate, NF 398-10 | 43.46 |
| Cellulose Acetate, NF 320S | 4.83 |
| Polyethylene Glycol 3350 | 4.83 |
| Purified Water, USP | n.a. |
| Acetone | n.a. |
| Total | 398 |

TABLE 9

| Component | Amount (mg) |
| --- | --- |
| Deutetrabenazine (micronized) | 24.00 |
| Butylated Hydroxyanisole, NF | 1.00 |
| Butylated Hydroxytoluene, NF | 0.40 |
| Polyethylene Oxide, NF (Polyox ® WSR N80) | 123.00 |
| Polyethylene Oxide, NF (FP) (Polyox ® WSR Coagulant, Fine Powder) | 68.62 |
| Methocel ® E5 Premium (Hypromellose 2910, USP) | 30.23 |
| Sodium Chloride, USP (Powder) | 30.23 |
| FD&C Red No. 40 Aluminum Lake HT 38%-42% | 0.32 |
| Magnesium Stearate, NF | 0.71 |
| Cellulose Acetate, NF (398-10) | 23.8 |
| Cellulose Acetate, NF (CA 320S) | 2.66 |
| Polyethylene Glycol 3350, NF | 2.66 |
| Hydroxypropyl Cellulose (Klucel ® LF) | 9.2 |
| Polysorbate 80 NF | 4 |
| Opadry ® II Gray 85F97586 | 9.6 |

TABLE 9-continued

| Component | Amount (mg) |
| --- | --- |
| Purified Water, USP | n.a. |
| Acetone | n.a. |
| Alcohol, USP (Ethyl Alcohol 190 proof) | n.a. |
| Total | 330.4 |

TABLE 10

| Component | Amount (mg) |
| --- | --- |
| Deutetrabenazine (micronized) | 24.00 |
| Butylated Hydroxyanisole, NF | 1 |
| Butylated Hydroxytoluene, NF | 0.4 |
| Polyethylene Oxide, NF (Polyox WSR N80) | 123.00 |
| Polyethylene Oxide, NF (FP) (Polyox WSR Coagulant, Fine Powder) | 71.7 |
| Methocel E5 Premium (Hypromellose 2910, USP) | 25.13 |
| Sodium Chloride, USP (Powder) | 27.9 |
| FD&C Red No. 40 Aluminum Lake HT 38%-42% | 0.3 |
| Magnesium Stearate, NF | 1 |
| Cellulose Acetate, NF (398-10) | 23.83 |
| Cellulose Acetate, NF (CA 320S) | 2.66 |
| Polyethylene Glycol 3350, NF | 2.66 |
| Hydroxypropyl Cellulose (Klucel LF) | 8.83 |
| Polysorbate 80 NF | 4 |
| Purified Water, USP | n.a. |
| Acetone | n.a. |
| Total | 316.4 |

TABLE 11

| Component | Amount (mg) |
| --- | --- |
| Deutetrabenazine (micronized) | 24.00 |
| Butylated Hydroxyanisole, NF | 0.5 |
| Butylated Hydroxytoluene, NF | 0.36 |
| Polyethylene Oxide, NF (Polyox WSR N80) | 123.4 |
| Polyethylene Oxide, NF (FP) (Polyox WSR Coagulant, Fine Powder) | 68.63 |
| Methocel E5 Premium (Hypromellose 2910, USP) | 41.86 |
| Sodium Chloride, USP (Powder) | 30.22 |
| FD&C Red No. 40 Aluminum Lake HT 38%-42% | 0.32 |
| Magnesium Stearate, NF | 0.7 |
| Cellulose Acetate, NF (398-10) | 27.03 |
| Cellulose Acetate, NF (CA 320S) | 3.02 |
| Polyethylene Glycol 3350, NF | 3.02 |
| Hydroxypropyl Cellulose (Klucel LF) | 9.2 |
| Opadry ® II Gray 85F97586 | 9.97 |
| Purified Water, USP | n.a. |
| Acetone | n.a. |
| Total | 342.2 |

TABLE 12

| Component | Amount (mg) |
| --- | --- |
| Deutetrabenazine (micronized) | 12.00 |
| Butylated Hydroxyanisole, NF | 1.00 |
| Butylated Hydroxytoluene, NF | 0.40 |
| Polyethylene Oxide, NF (Polyox ® WSR N80) | 132.6 |
| Polyethylene Oxide, NF (FP) (Polyox ® WSR Coagulant, Fine Powder) | 68.63 |
| Methocel ® E5 Premium (Hypromellose 2910, USP) | 30.25 |
| Sodium Chloride, USP (Powder) | 30.22 |
| FD&C Red No. 40 Aluminum Lake HT 38%-42% | 0.32 |
| Magnesium Stearate, NF | 0.72 |
| Cellulose Acetate, NF (398-10) | 23.8 |
| Cellulose Acetate, NF (CA 320S) | 2.66 |
| Polyethylene Glycol 3350, NF | 2.66 |

TABLE 12-continued

| Component | Amount (mg) |
|---|---|
| Hydroxypropyl Cellulose (Klucel ® LF) | 9.2 |
| Polysorbate 80 NF | 4 |
| Opadry ® II Gray 85F97586 | 9.6 |
| Purified Water, USP | n.a. |
| Acetone | n.a. |
| Alcohol, USP (Ethyl Alcohol 190 proof) | n.a. |
| Total | 328 |

TABLE 13

| Component | Amount (mg) |
|---|---|
| Deutetrabenazine | 12.00 |
| Butylated Hydroxyanisole | 0.5 |
| Butylated Hydroxytoluene | 0.36 |
| Polyethylene Oxide (Polyox WSR N80) | 123.40 |
| Polyethylene Oxide (Polyox WSR Coagulant) | 68.63 |
| Hypromellose 2910 (MethocelTM E5 Premium) | 50.44 |
| Sodium Chloride | 30.22 |
| FD&C Red No. 40[1] | 0.32 |
| Magnesium Stearate | 0.70 |
| Cellulose Acetate (398-10) | 27.03 |
| Cellulose Acetate (CA 320S) | 3.02 |
| Polyethylene Glycol 3350 | 3.02 |
| Hydroxypropyl Cellulose | 9.2 |
| Opadry ® II 85F175047 Grey | — |
| Opadry ® II 85F99094 Blue | 9.87 |
| Opadry ® II 85F100129 Purple | — |
| Ink, Black (Opacode ® Black S-1-17823) | n.a. |
| Purified Water[2] | n.a. |
| Acetone[2] | n.a. |
| Ethanol[2] | n.a. |
| Isopropyl Alcohol[2] | n.a. |
| Total | 338.7 |

[1]FD&C Red No. 40 is listed in FDA's Inactive Ingredients Database and is within the recommended limit.
[2]Water, Acetone, Ethanol and Isopropyl Alcohol are used to manufacture the tablets but are removed during processing.

TABLE 14

| Component | Amount (mg) |
|---|---|
| Deutetrabenazine (micronized) | 6.00 |
| Butylated Hydroxyanisole, NF | 1.00 |
| Butylated Hydroxytoluene, NF | 0.40 |
| Polyethylene Oxide, NF (Polyox ® WSR N80) | 137.4 |
| Polyethylene Oxide, NF (FP) (Polyox ® WSR Coagulant, Fine Powder) | 68.63 |
| Methocel ® E5 Premium (Hypromellose 2910, USP) | 30.25 |
| Sodium Chloride, USP (Powder) | 30.22 |
| FD&C Red No. 40 Aluminum Lake HT 38%-42% | 0.32 |
| Magnesium Stearate, NF | 0.72 |
| Cellulose Acetate, NF (398-10) | 23.8 |
| Cellulose Acetate, NF (CA 320S) | 2.66 |
| Polyethylene Glycol 3350, NF | 2.66 |
| Hydroxypropyl Cellulose (Klucel ® LF) | 9.2 |
| Polysorbate 80 NF | 4 |
| Opadry ® II Gray 85F97586 | 9.6 |
| Purified Water, USP | n.a. |
| Acetone | n.a. |
| Alcohol, USP (Ethyl Alcohol 190 proof) | n.a. |
| Total | 326.8 |

TABLE 15

| Component | Amount (mg) |
|---|---|
| Deutetrabenazine | 6.00 |
| Butylated Hydroxyanisole | 0.5 |

TABLE 15-continued

| Component | Amount (mg) |
|---|---|
| Butylated Hydroxytoluene | 0.36 |
| Polyethylene Oxide (Polyox WSR N80) | 123.40 |
| Polyethylene Oxide (Polyox WSR Coagulant) | 68.63 |
| Hypromellose 2910 (MethocelTM E5 Premium) | 54.74 |
| Sodium Chloride | 30.22 |
| FD&C Red No. 40[1] | 0.32 |
| Magnesium Stearate | 0.70 |
| Cellulose Acetate (398-10) | 27.03 |
| Cellulose Acetate (CA 320S) | 3.02 |
| Polyethylene Glycol 3350 | 3.02 |
| Hydroxypropyl Cellulose | 9.2 |
| Opadry ® II 85F175047 Grey | 9.53 |
| Opadry ® II 85F99094 Blue | — |
| Opadry ® II 85F100129 Purple | — |
| Ink, Black (Opacode ® Black S-1-17823) | n.a. |
| Purified Water[2] | n.a. |
| Acetone[2] | n.a. |
| Ethanol[2] | n.a. |
| Isopropyl Alcohol[2] | n.a. |
| Total | 337.0 |

Example 2—Single Dose Bioavailability Assessment

Osmotic dosage forms containing 24 mg deutetrabenazine were produced as disclosed in Example 1 and studied in a single dose pharmacokinetic study.

The primary objective was to assess the comparative bioavailability (BA) of deutetrabenazine and deuterated α- and β-dihydrotetrabenazine (deuHTBZ) metabolites following a single administration of 24 mg, once daily (q.d.) osmotic formulation (Test) compared to a single 12 mg AUSTEDO® tablet administered twice, 12 hours apart (b.i.d), under fasted conditions.

Study Population and Number of Subjects: The study included healthy male and female non-smoking subjects, aged 18 through 45 years. A total of 8 healthy subjects (4 per sequence) were enrolled in this study.

Duration of Subject Participation: The study included a screening period of 4 weeks (period 1), an open label treatment period with the test formulation (Test2A) and the reference formulation (R) (period 2), and a follow-up visit at least 1 day later (period 3).

Treatments:

Treatment Sequence A:

Day 1—administration of Test2A.

Days 2-3—at least 6 hours wash out of Test2A followed by administration of R.

Treatment Sequence B:

Day 1—administration of R

Days 2-3—at least 6 hours wash out of R, followed by administration of Test2A.

The primary objective was addressed using the following parameters:

maximum observed concentration ($C_{max}$)

area under the plasma concentration-time (AUC) from time 0 to the time of the last measurable plasma concentration (AUC0-t)

AUC extrapolated to infinity (AUC0-∞)

AUC from time 0 to 24 hours post dose (AUC0-24h)

Analyses

AUC0-t, AUC0-∞, and AUC0-24h were calculated using the trapezoidal rule. The $C_{max}$, AUC0-t, AUC0-∞, and AUC0-24h data was natural log-transformed prior to the statistical analysis. Comparisons of $C_{max}$, AUC0-t, AUC0-∞, and AUC0-24h between treatments (T2A vs R) was be carried out using a separate parametric analysis of variance (ANOVA) model with fixed effect terms for sequence, period, treatment group, and a random effect of subject within sequence. The difference between the reference formulation (R) and the test formulation (Test2A) was evaluated by constructing 90% confidence intervals for the Test/Reference ratios, based on the least-square means from the ANOVA for the log-transformed $C_{max}$, AUC0-t, AUC0-∞ and AUC0-24h. The treatment difference and the associated 90% confidence interval estimated from the ANOVA on the log scale was back-transformed to obtain the estimated ratio of geometric means between treatment groups and the 90% confidence interval for this ratio.

Figure 3A:
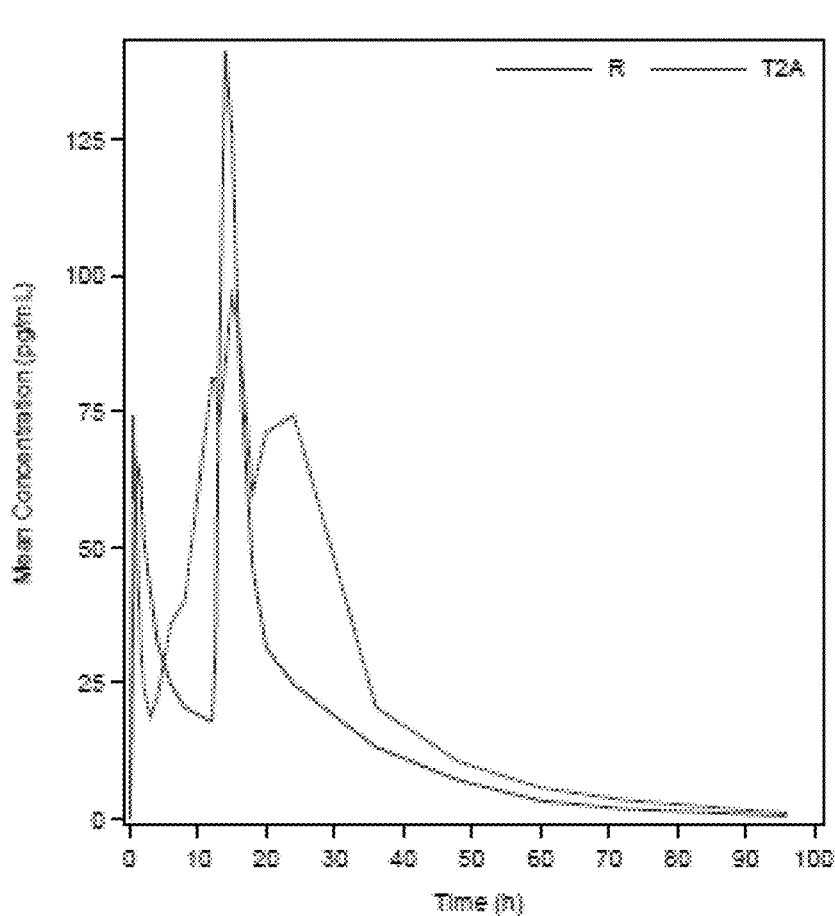
FIG. 3a and FIG. 3b are graphs showing concentration (pg/mL) of deutetrabenazine vs. time (hours, "h") in subjects administered 12 mg AUSTEDO® tablet bid ("R") or an osmotic dosage form containing 24 mg deutetrabenazine qd ("T2A").
Figure 3B:
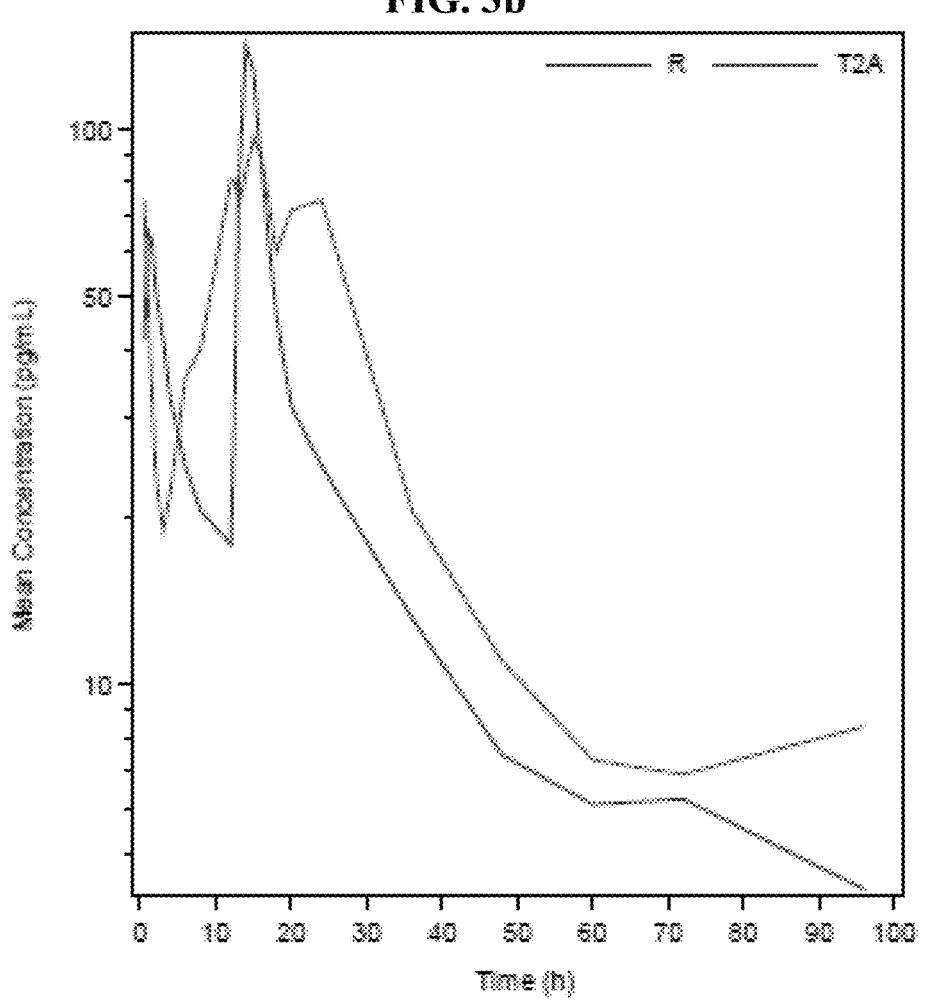

FIG. 3a and FIG. 3b show the results of the R treatment compared to Test2A treatment (mean concentration of deutetrabenazine vs. time) direct scale and log scale, respectively. Table 14, below, provides the specified pK parameters observed for deutetrabenazine with respect to Test2A compared to R.

TABLE 14

| Comparison | pK Parameter | Geometric LS Mean Test2A | Geometric LS Mean R | Geometric LS Mean Ratio (Test2A/R (%) | 90% C.I. of Geometric LS Mean Ratio (Test2A/R) (%) |
|---|---|---|---|---|---|
| Test2A vs. R | AUC 0-24 h (h*pg/mL) | 873.3 | 898.1 | 97.2 | (78.8, 119.9) |
| | AUC Infinity Obs (h*pg/mL) | 1656 | 1433.7 | 115.5 | (94.6, 141.0) |
| | AUC[0-t] (h*pg/mL) | 1492.8 | 1287.4 | 115.9 | (94.2, 142.7) |
| | Max Conc (pg/mL) | 97.7 | 137 | 71.3 | (55.0, 92.5) |

Figure 4A:
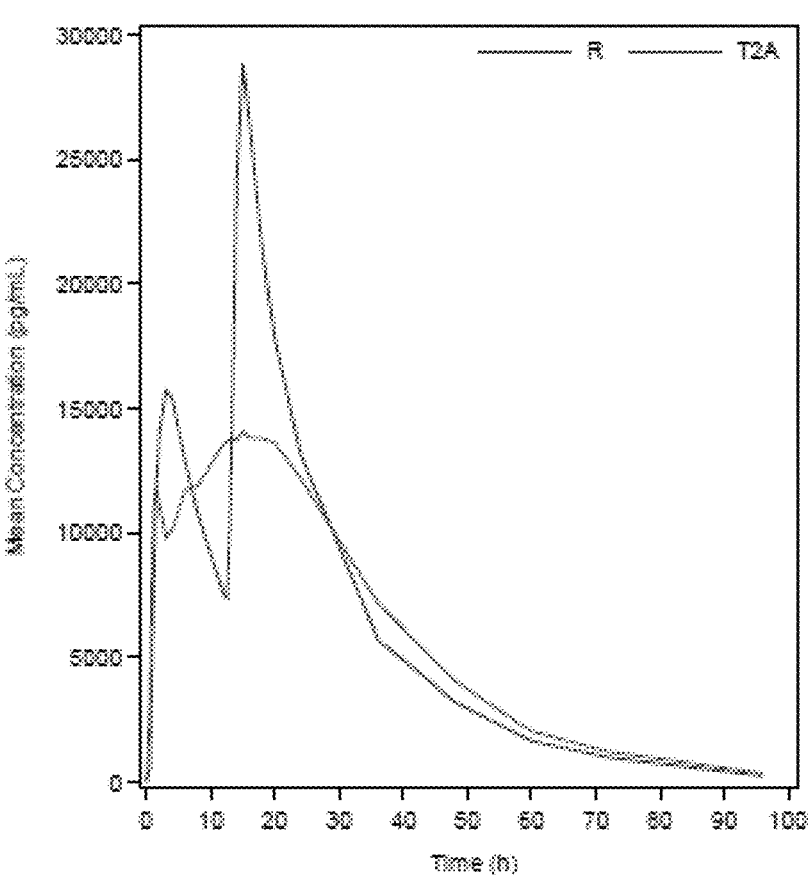
FIG. 4a and FIG. 4B are graphs showing concentration (pg/mL) of α- and β-deuHTBZ (total deuHTBZ) vs. time (hours, "h") in subjects administered 12 mg AUSTEDO® tablet bid ("R") or an osmotic dosage form containing 24 mg deutetrabenazine qd ("T2A").
Figure 4B:
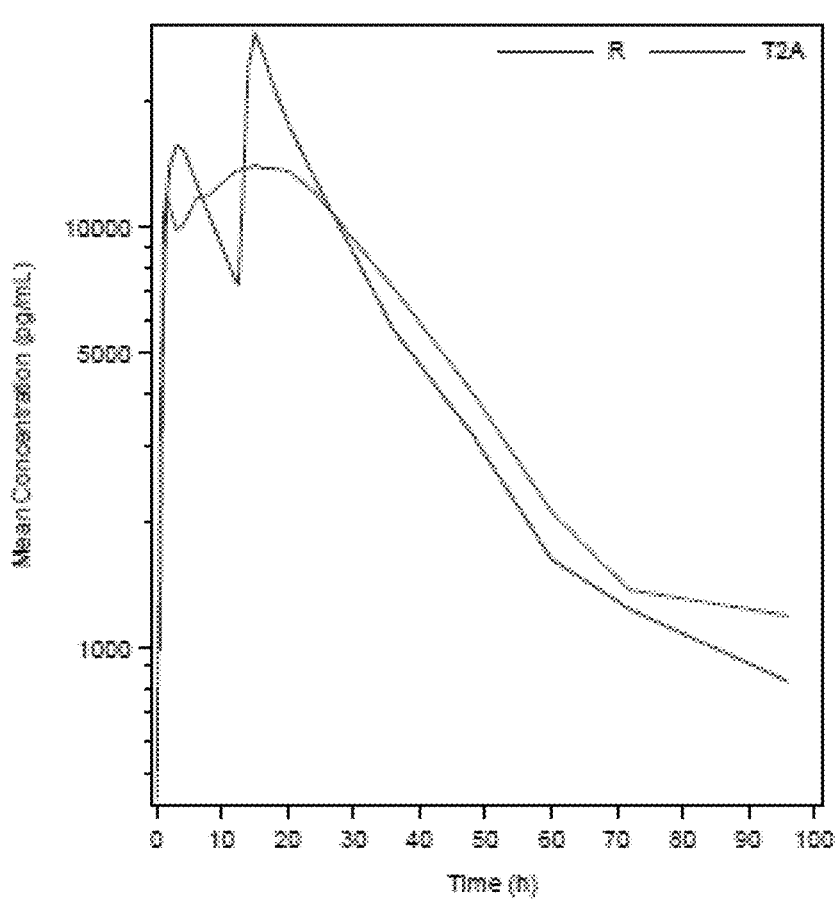

FIG. 4a and FIG. 4b show the metabolite data for the treatment using R compared to Test2A (mean concentration of total deuHTBZ vs. time), direct scale and log scale, respectively.

Table 15, below, provides the specified pK parameters observed for total deuHTBZ for the Test2A compared to R.

TABLE 15

| Comparison | pK Parameter | Geometric LS Mean Test2A (total deuHTBZ) | Geometric LS Mean R (total deuHTBZ) | Geometric LS Mean Ratio (Test2A/R) (%) | 90% C.I. of Geometric LS Mean Ratio (Test2A/R) (%) |
|---|---|---|---|---|---|
| Test2A vs. R | AUC 0-24 h (h*pg/mL) | 267927.4 | 326315.1 | 82.1 | (77.3, 87.3) |
| | AUC Infinity Obs (h*pg/mL) | 466549.9 | 504708.5 | 92.4 | (86.0, 99.3) |
| | AUC[0-t] (h*pg/mL) | 457030.3 | 495271.0 | 92.3 | (85.9, 99.2) |
| | Max Conc (pg/mL) | 14748.2 | 29180.0 | 50.5 | (47.0, 54.4) |

As shown in Tables 14 and 15, a once-daily dose of Test2A provided acceptable deuHTBZ plasma concentrations observed for the reference. The osmotic dosage forms disclosed herein are administered once daily and provide acceptable treatment effects to that of AUSTEDO® and also have no safety concerns.

The results of this study, having a crossover design, further show that a patient can be safely and effectively transitioned from a twice daily (two divided doses) administration of deutetrabenazine tablets, to a once daily osmotic dosage form. The results of this study, having a crossover design, also show that a patient can be safely and effectively transitioned from a once daily osmotic dosage form to a twice daily administration of deutetrabenazine tablet (two divided doses).

Example 3—Multiple Dose Bioavailability Assessment

Osmotic dosage form containing 24 mg of deutetrabenazine were produced as disclosed in Example 1 and studied in an open label, randomized, multiple-dose, 2-way crossover study in healthy volunteers.

The primary objective was to assess the bioequivalence (BE) of administration of Test2A, once daily (qd) compared to bid administration of R, under fasted or fed conditions.

Treatment included 7 days repeated dosing of Test2A once daily versus 7 days repeated dosing of R, bid.

Qualified models were used to predict the steady state, AUCt, $C_{max}$, tmax, Cmin, Cav for deutetrabenazine and deuHTBZ concentrations.

Table 16, below, provides simulation results for steady state pK parameters for deutetrabenazine with respect to Test2A compared to R as well as pK parameters for total deuHTBZ for the Test2A compared to R.

TABLE 16

| Analyte | Comparison | PK Parameter (Mean) | Test2A | R | Test2A/R Ratio |
|---|---|---|---|---|---|
| Deutetrabenazine | Test2A vs. R | $AUC_{0-24 h}$ [pg*h/mL] | 2390 | 1784 | 1.34 |
| Deutetrabenazine | Test2A vs. R | $C_{max}$ [pg/mL] | 155 | 134 | 1.16 |
| Total deuHTBZ | Test2A vs. R | $AUC_{0-24 h}$ [pg*h/mL] | 556826 | 519835 | 1.07 |
| Total deuHTBZ | Test2A vs. R | $C_{max}$ [pg/mL] | 28695 | 28485 | 1.01 |

Study Results

Administration of the treatments, Test2A and R, resulted in reproducible concentration-time profiles for all analytes.

The primary objective of demonstrating bioequivalence (BE) for $AUC_{0-24h,ss}$ for deutetrabenazine and the deuHTBZ (individually and as a sum) between Test2A and R formulations was met. The geometric LS mean ratio for $AUC_{0\text{-}24h,ss}$ was 115.15% for deutetrabenazine and 95.05% for total deuHTBZ.

The results of this study, having a crossover design, further show that a patient can be safely and effectively transitioned from a twice daily administration of deutetrabenazine tablet, to a once daily osmotic dosage form. The results of this study, having a crossover design, further show that a patient can be safely and effectively transitioned from a once daily osmotic dosage form to a twice daily administration of deutetrabenazine tablet.

Example 4: Food Effect Study

Osmotic dosage forms containing 24 mg deutetrabenazine were produced as disclosed in Example 1 and studied in an open label, randomized, 3-period, 3-treatment, 6-sequence, crossover study, to assess the comparative bioavailability of deutetrabenazine and deuHTBZ in the fed compared to the fasted state, following a single administration of 24 mg, once daily (qd) osmotic formulation.

Figure 5:
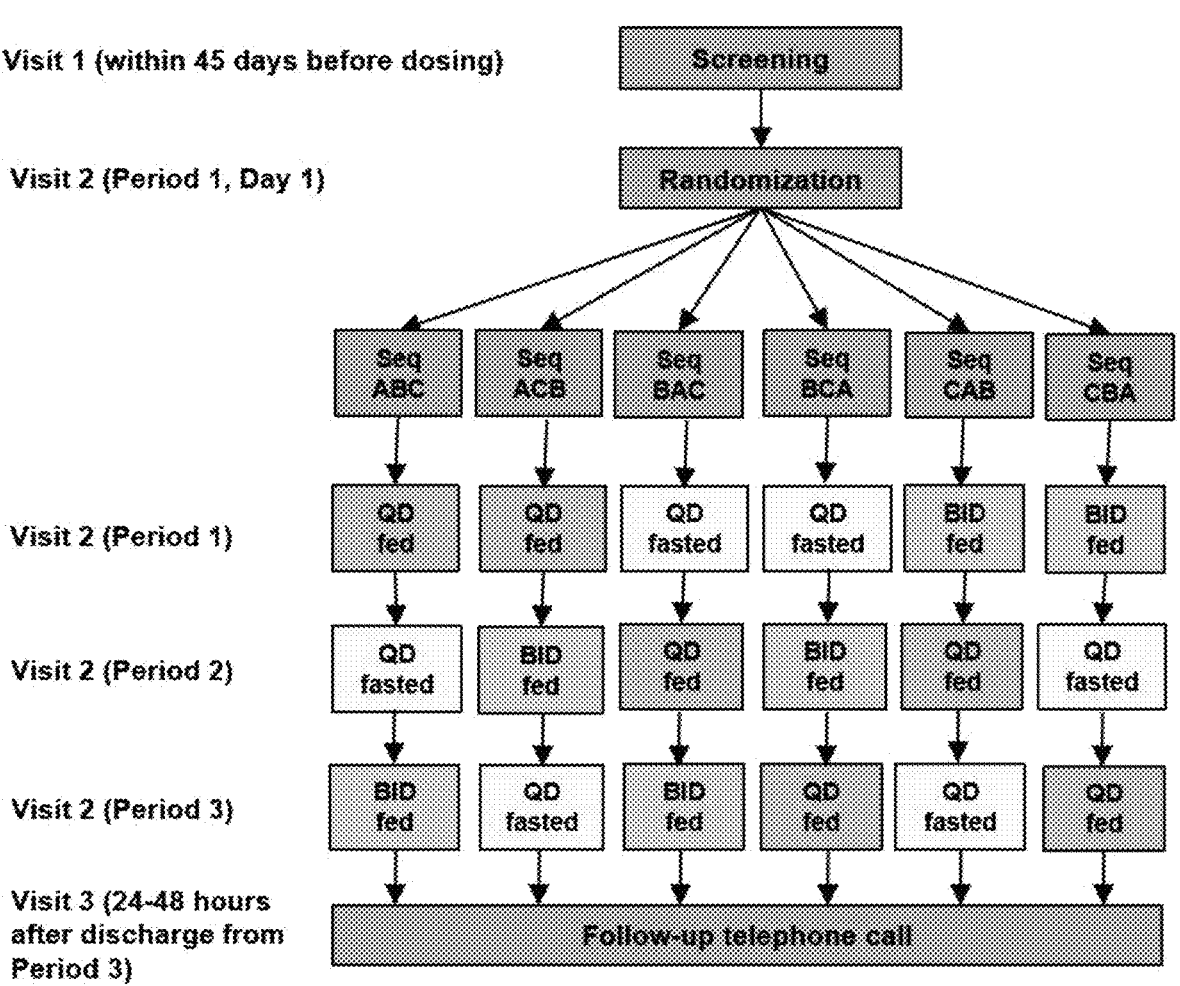
FIG. 5 is a diagram summarizing the food effect study described in Example 4.

Treatment included:

Subjects were randomly assigned to receive 3 treatments: Test2A in fed state (QD fed), Test2A in the fasted state (QD fasted), and R, 12 hours apart in fed state [twice daily (BID) fed] in 1 of 6 treatment sequences, as depicted in FIG. 5.

There was at least a 6-day washout period between the first administration in a period and the first administration in the following period. Treatments were orally administered to subjects, in a seated position, in the morning on the first day (day 1) of each administration period. The second dose of R in the BID fed group was administered exactly 12 hours after the morning dose.

All subjects fasted overnight for at least 10 hours before the first dose during each period. A standardized high-calorie, high-fat breakfast (containing 800 to 1000 kilocalories [kcal] with 50% fat) was served 30 minutes before the first dose to subjects receiving R BID fed or Test2A tablet fed. A standardized dinner was served 30 minutes before the second dose for R BID fed or the corresponding time for Test2A tablet fed.

Blood samples for pharmacokinetic analysis were collected prior to dosing and up to 96 hours after dosing in all treatment periods $AUCt$, $C_{max}$, tmax, Cmin, Cav for deutetrabenazine and deuHTBZ were analyzed.

Results

For all analytes, variability for the Test2A fed treatment was overall similar to that of the Test2A fasted treatment, indicating that administration of a single 24 mg tablet in the fed state, as opposed to a single 24 mg tablet in the fasted state, does not greatly increase the pharmacokinetic variability for the metabolites Following oral administration of a single 24 mg QD osmotic tablet under fed and fasted conditions, all analytes met the BE criteria. No significant food effect on PK was evident, and the 24 mg QD tablet can thus be administered with or without food.

A single dose of 24 mg deutetrabenazine QD osmotic tablet in either the fed or fasted state, as well the 12 mg deutetrabenazine tablet (fed state) administered twice daily, appeared safe and well tolerated in healthy subjects.

What is claimed:

1. A method of transitioning a human subject being treated with a total daily dose of deutetrabenazine twice daily (bid) to the total daily dose as a deutetrabenazine once daily for control of abnormal involuntary movement, comprising:

a) administering to the human subject a last dose of the deutetrabenazine twice daily; and b) the next day, administering to the human subject the total daily dose as a deutetrabenazine once daily osmotic dosage form, wherein the osmotic dosage form comprises:

a. a tablet core comprising an active layer and a push layer, wherein the active layer comprises an amount of deutetrabenazine microparticles and an active layer control release agent, and wherein the push layer comprises an osmotic agent and a push layer control release agent, and an optional tablet seal coat on the outer surface of the tablet core;

b. a semipermeable layer surrounding the tablet core;

c. a port extending through the semipermeable layer into the tablet core; and d. an immediate release coating external to the semipermeable layer comprising a second amount of deutetrabenazine microparticles, wherein the dosage comprises from about 6 mg to about 48 mg deutetrabenazine in the form of deutetrabenazine microparticles and wherein about 70%-80% of the total amount of deutetrabenazine microparticles present in the dosage form is present within the active layer and wherein about 20%-30% of the total amount of deutetrabenazine microparticles present in the dosage form, is present within the immediate release coating;

wherein the deutetrabenazine microparticles have a $D_{90}$ of 15 μm, a $D_{50}$ 10 μm, and/or a $D_{10}$ of 3 μm, and wherein the control of the abnormal involuntary movement is maintained during the transitioning from the last dose of deutetrabenazine twice daily to the deutetrabenazine once daily osmotic dosage form.

2. The method of claim 1, wherein the total daily dose of deutetrabenazine is from 12 mg to 48 mg; or 12 mg; or 18 mg; or 24 mg; or 30 mg; or 36 mg; or 42 mg; or 48 mg.

3. The method of claim 1, wherein the abnormal involuntary movement is chorea, akathisia, dyskinesia, tremor, tic, chorea associated with Huntington's disease, tardive dyskinesia, a tic associated with Tourette syndrome, Parkinson's disease levodopa-induced dyskinesia, or dyskinesia in cerebral palsy.

4. The method of claim 1, wherein the total daily dose of deutetrabenazine once daily is administered with or without food.

5. A method of transitioning a human subject being treated with a daily amount of tetrabenazine to a once daily amount of deutetrabenazine, for control of abnormal involuntary movement from, comprising:

a) administering the last dose of tetrabenazine; and b) the next day, administering to the subject a once daily deutetrabenazine osmotic dosage form, wherein the control of the abnormal involuntary movement is maintained during the transitioning from the last dose of tetrabenazine to the once daily deutetrabenazine dosage form wherein the daily amount of tetrabenazine is 25 mg and the once daily amount of deutetrabenazine is 12 mg; or wherein the daily amount of tetrabenazine is 37.5 mg and the once daily amount of deutetrabenazine is 18 mg; or wherein the daily amount of tetrabenazine is 50 mg and the once daily amount of deutetrabenazine is 24 mg; or wherein the daily amount of tetrabenazine is 62.5 mg and the once daily amount of deutetrabenazine is 30 mg; or wherein the daily amount of tetrabenazine is 75 mg and the once daily amount of deutetrabenazine is 36 mg; or wherein the daily amount of tetrabenazine is 87.5 mg and the once daily amount of deutetrabenazine is 42 mg; or wherein the daily amount of tetrabenazine is 100 mg and the once daily amount of deutetrabenazine is 48 mg; and wherein the osmotic dosage form comprises:

a. a tablet core comprising an active layer and a push layer, wherein the active layer comprises an amount of deutetrabenazine microparticles and an active layer control release agent, and wherein the push layer comprises an osmotic agent and a push layer control release agent, and an optional tablet seal coat on the outer surface of the tablet core;

b. a semipermeable layer surrounding the tablet core;

c. a port extending through the semipermeable layer into the tablet core; and d. an immediate release coating external to the semipermeable layer comprising a second amount of deutetrabenazine microparticles, wherein the dosage comprises from about 6 mg to about 48 mg deutetrabenazine in the form of deutetrabenazine microparticles and wherein about 70%-80% of the total amount of deutetrabenazine microparticles present in the dosage form is present within the active layer and wherein about 20%-30% of the total amount of deutetrabenazine microparticles present in the dosage form, is present within the immediate release coating, and wherein the deutetrabenazine microparticles have a $D_{90}$ of 15 μm, a $D_{50}$ 10 μm, and/or a $D_{10}$ of 3 μm.

6. The method of claim 5, wherein the abnormal involuntary movement is chorea, akathisia, dyskinesia, tremor, tic, chorea associated with Huntington's disease, tardive dyskinesia, a tic associated with Tourette syndrome, Parkinson's disease levodopa-induced dyskinesia or dyskinesia in cerebral palsy.

7. The method of claim 5, wherein the once daily deutetrabenazine dosage form, is administered with or without food.

* * * * *